(12) United States Patent
Wilson et al.

(10) Patent No.: US 12,065,649 B2
(45) Date of Patent: Aug. 20, 2024

(54) PATTERN RECOGNITION RECEPTOR AGONIST PRODRUGS AND METHODS OF USE THEREOF

(71) Applicant: Vanderbilt University, Nashville, TN (US)

(72) Inventors: John T. Wilson, Nashville, TN (US); Christian Palmer, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 650 days.

(21) Appl. No.: 16/961,205

(22) PCT Filed: Jan. 9, 2019

(86) PCT No.: PCT/US2019/012929
§ 371 (c)(1),
(2) Date: Jul. 9, 2020

(87) PCT Pub. No.: WO2019/140001
PCT Pub. Date: Jul. 18, 2019

(65) Prior Publication Data
US 2020/0370052 A1 Nov. 26, 2020

Related U.S. Application Data

(60) Provisional application No. 62/615,370, filed on Jan. 9, 2018.

(51) Int. Cl.
*C12N 15/113* (2010.01)
*A61K 47/60* (2017.01)

(52) U.S. Cl.
CPC .......... *C12N 15/1138* (2013.01); *A61K 47/60* (2017.08)

(58) Field of Classification Search
CPC ............................ C12N 15/1138; A61K 47/60
See application file for complete search history.

(56) References Cited

U.S. PATENT DOCUMENTS

| | | | |
|---|---|---|---|
| 9,695,212 B2 | 7/2017 | Dubensky, Jr. et al. | |
| 10,696,985 B1* | 6/2020 | Wilson | C12N 15/87 |
| 2014/0273215 A1* | 9/2014 | Guo | A61K 47/6923 |
| | | | 435/375 |
| 2014/0287023 A1 | 9/2014 | Hiscott et al. | |

OTHER PUBLICATIONS

Mishra, et al., PEGylation in anti-cancer therapy: An overview, Asian Jouranl of Pharmaceutical Science, Sep. 14, 2015, vol. 11, No. 3, p. 337-348.
Heidel, et al., Cyclodextrin-Containing Polymers: Versatile Platforms of Drug Delivery Materials, Journal of Drug Delivery, 2012, vol. 2012, Article ID 262731, p. 1-17.
Akira, S.; Uematsu, S.; Takeuchi, O., Pathogen Recognition and Innate Immunity. Cell 2006, 124 (4), 783-801.
Mancini, R. J.; Stutts, L.; Ryu, K. A.; Tom, J. K.; Esser-Kahn, A. P., Directing the immune system with chemical compounds. ACS Chem Biol 2014, 9 (5), 1075-85.
Lynn, G. M.; Laga, R.; Darrah, P. A.; Ishizuka, A. S.; Balaci, A. J.; Dulcey, A. E.; Pechar, M.; Pola, R.; Gerner, M. Y.; Yamamoto, A.; Buechler, C. R.; Quinn, K. M.; Smelkinson, M. G.; Vanek, O.; Cawood, R.; Hills, T.; Vasalatiy, O.; Kastenmuller, K.; Francica, J. R.; Stutts, L.; Tom, J. K.; Ryu, K. A.; Esser-Kahn, A. P.; Etrych, T.; Fisher, K. D.; Seymour, L. W.; Seder, R. A., In vivo characterization of the physicochemical properties of polymer-linked TLR agonists that enhance vaccine immunogenicity. Nat Biotechnol 2015, 33 (11), 1201-10.
Gutjahr, A.; Tiraby, G.; Perouzel, E.; Verrier, B.; Paul, S., Triggering Intracellular Receptors for Vaccine Adjuvantation. Trends Immunol 2016, 37 (9), 573-87.
Maisonneuve, C.; Bertholet, S.; Philpott, D. J.; De Gregorio, E., Unleashing the potential of NOD- and Toll-like agonists as vaccine adjuvants. Proceedings of the National Academy of Sciences of the United States of America 2014, 111 (34), 12294-12299.
Van den Boorn, J. G.; Hartmann, G., Turning Tumors into Vaccines: Co-opting the Innate Immune System. Immunity 2013.
Moynihan, K. D.; Irvine, D. J., Roles for Innate Immunity in Combination Immunotherapies. Cancer Res 2017, 77 (19), 5215-5221.
Fiuza, C.; Suffredini, A. F., Human models of innate immunity: local and systemic inflammatory responses. Journal of Endotoxin Research 2001, 7 (5), 385-388.
Copin, R.; Vitry, M. A.; Hanot Mambres, D.; Machelart, A.; De Trez, C.; Vanderwinden, J. M.; Magez, S.; Akira, S.; Ryffel, B.; Carlier, Y.; Letesson, J. J.; Muraille, E., In situ microscopy analysis reveals local innate immune response developed around *Brucella* infected cells in resistant and susceptible mice. PLoS Pathog 2012, 8 (3), e1002575.
Liang, F.; Lore, K., Local innate immune responses in the vaccine adjuvant-injected muscle. Clin Transl Immunology 2016, 5 (4), e74.
Tang, D. L.; Kang, R.; Coyne, C. B.; Zeh, H. J.; Lotze, M. T., PAMPs and DAMPs: signal 0s that spur autophagy and immunity. Immunological Reviews 2012, 249 (1600-065X (Electronic)), 158-175.
Appelbe, O. K.; Moynihan, K. D.; Flor, A.; Rymut, N.; Irvine, D. J.; Kron, S. J., Radiation-enhanced delivery of systemically administered amphiphilic-CpG oligodeoxynucleotide. J Control Release 2017, 266, 248-255.
Dudek, A. Z.; Yunis, C.; Harrison, L. I.; Kumar, S.; Hawkinson, R.; Cooley, S.; Vasilakos, J. P.; Gorski, K. S.; Miller, J. S., First in human phase I trial of 852A, a novel systemic toll-like receptor 7 agonist, to activate innate immune responses in patients with advanced cancer. Clin Cancer Res 2007, 13 (23), 7119-25.

(Continued)

*Primary Examiner* — J. E. Angell
(74) *Attorney, Agent, or Firm* — Michael Best & Friedrich LLP

(57) ABSTRACT

Provided herein are a selective pattern recognition receptor (PRR) agonist and a method of selectively activating a PRR. The selective PRR agonist includes a nucleic acid agonist and a macromolecule conjugated to the nucleic acid agonist. The method includes administering the selective PRR agonist to a subject, and cleaving at least a portion of the macromolecule conjugated to the nucleic acid agonist, the cleaving of at least a portion of the macromolecule permitting the agonist to bind a PRR.

18 Claims, 7 Drawing Sheets
Specification includes a Sequence Listing.

(56) References Cited

OTHER PUBLICATIONS

Campanelli, A.; Krischer, J.; Saurat, J. H., Topical application of imiquimod and associated fever in children. J Am Acad Dermatol 2005, 52 (1), E1.
Savage, P.; Horton, V.; Moore, J.; Owens, M.; Witt, P.; Gore, M. E., A phase I clinical trial of imiquimod, an oral interferon inducer, administered daily. Br J Cancer 1996, 74 (9), 1482-6.
Engel, A. L.; Holt, G. E.; Lu, H., The pharmacokinetics of Toll-like receptor agonists and the impact on the immune system. Expert Rev Clin Pharmacol 2011, 4 (2), 275-89.
Vasou, A.; Sultanoglu, N.; Goodbourn, S.; Randall, R. E.; Kostrikis, L. G., Targeting Pattern Recognition Receptors (PRR) for Vaccine Adjuvantation: From Synthetic PRR Agonists to the Potential of Defective Interfering Particles of Viruses. Viruses 2017, 9 (7).
Broz, P.; Monack, D. M., Newly described pattern recognition receptors team up against intracellular pathogens. Nature Reviews Immunology 2013, 13 (8), 551-565.
Iwasaki, A.; Medzhitov, R., Toll-like receptor control of the adaptive immune responses. Nat Immunol 2004, 5 (10), 987-95.
Kuai, R.; Ochyl, L. J.; Bahjat, K. S.; Schwendeman, A.; Moon, J. J., Designer vaccine nanodiscs for personalized cancer immunotherapy. Nat Mater 2017, 16 (4), 489-496.
Tom, J. K.; Dotsey, E. Y.; Wong, H. Y.; Stutts, L.; Moore, T.; Davies, D. H.; Felgner, P. L.; Esser-Kahn, A. P., Modulation of Innate Immune Responses via Covalently Linked TLR Agonists. ACS Cent Sci 2015, 1 (8), 439-448.
Liu, H.; Moynihan, K. D.; Zheng, Y.; Szeto, G. L.; Li, A. V.; Huang, B.; Van Egeren, D. S.; Park, C.; Irvine, D. J., Structure-based programming of lymph-node targeting in molecular vaccines. Nature 2014, 507 (7493), 519-522.
Corrales, L.; Glickman, L. H.; McWhirter, S. M.; Kanne, D. B.; Sivick, K. E.; Katibah, G. E.; Woo, S. R.; Lemmens, E.; Banda, T.; Leong, J. J.; Metchette, K.; Dubensky, T. W., Jr.; Gajewski, T. F., Direct Activation of STING in the Tumor Microenvironment Leads to Potent and Systemic Tumor Regression and Immunity. Cell Rep 2015, 11 (7), 1018-30.
Zhang, P.; Chiu, Y. C.; Tostanoski, L. H.; Jewell, C. M., Polyelectrolyte Multilayers Assembled Entirely from Immune Signals on Gold Nanoparticle Templates Promote Antigen-Specific T Cell Response. ACS Nano 2015, 9 (6), 6465-77.
He, S.; Mao, X.; Sun, H.; Shirakawa, T.; Zhang, H.; Wang, X., Potential therapeutic targets in the process of nucleic acid recognition: opportunities and challenges. Trends Pharmacol Sci 2015, 36 (1), 51-64.
Schlee, M., Master sensors of pathogenic RNA—RIG-I like receptors. Immunobiology 2013, 218 (11), 1322-35.
Kell, A. M.; Gale, M., Jr., RIG-I in RNA virus recognition. Virology 2015, 479-480, 110-21.
Hornung, V.; Ellegast, J.; Kim, S.; Brzozka, K.; Jung, A.; Kato, H.; Poeck, H.; Akira, S.; Conzelmann, K. K.; Schlee, M.; Endres, S.; Hartmann, G., 5'-Triphosphate RNA Is the Ligand for RIG-I. Science 2006, 314 (5801), 994-997.
Goulet, M.- L.; Olagnier, D.; Xu, Z.; Paz, S.; Belgnaoui, S. M.; Lafferty, E. I.; Janelle, V.; Arguello, M.; Paquet, M.; Ghneim, K.; Richards, S.; Smith, A.; Wilkinson, P.; Cameron, M.; Kalinke, U.; Qureshi, S.; Lamarre, A.; Haddad, E. K.; Sekaly, R. P.; Peri, S.; Balachandran, S.; Lin, R.; Hiscott, J., Systems analysis of a RIG-I agonist inducing broad spectrum inhibition of virus infectivity. PLoS pathogens 2013, 9 (4), e1003298.
Kohlway, A.; Luo, D.; Rawling, D. C.; Ding, S. C.; Pyle, A. M., Defining the functional determinants for RNA surveillance by RIG-I. EMBO reports 2013, 14 (9), 772-779.
Parker, B. S.; Rautela, J.; Hertzog, P. J., Antitumour actions of interferons: implications for cancer therapy. Nat Rev Cancer 2016, 16 (3), 131-44.
Harlin, H.; Meng, Y.; Peterson, A. C.; Zha, Y.; Tretiakova, M.; Slingluff, C.; McKee, M.; Gajewski, T. F., Chemokine expression in melanoma metastases associated with CD8+ T-cell recruitment. Cancer Res 2009, 69 (7), 3077-85.

Gajewski, T. F., The Next Hurdle in Cancer Immunotherapy: Overcoming the Non-T-Cell-Inflamed Tumor Microenvironment. Semin Oncol 2015, 42 (4), 663-71.
Ellermeier, J.; Wei, J.; Duewell, P.; Hoves, S.; Stieg, M. R.; Adunka, T.; Noerenberg, D.; Anders, H. J.; Mayr, D.; Poeck, H.; Hartmann, G.; Endres, S.; Schnurr, M., Therapeutic Efficacy of Bifunctional siRNA Combining TGF-beta1 Silencing with RIG-I Activation in Pancreatic Cancer. Cancer Research 2013, 73 (6), 1709-1720.
Duewell, P.; Steger, A.; Lohr, H.; Bourhis, H.; Hoelz, H.; Kirchleitner, S. V.; Stieg, M. R.; Grassmann, S.; Kobold, S.; Siveke, J. T.; Endres, S.; Schnurr, M., RIG-I-like helicases induce immunogenic cell death of pancreatic cancer cells and sensitize tumors toward killing by CD8(+) T cells. Cell Death Differ 2014, 21 (12), 1825-37.
Poeck, H.; Besch, R.; Maihoefer, C.; Renn, M.; Tormo, D.; Morskaya, S. S.; Kirschnek, S.; Gaffal, E.; Landsberg, J.; Hellmuth, J.; Schmidt, A.; Anz, D.; Bscheider, M.; Schwerd, T.; Berking, C.; Bourquin, C.; Kalinke, U.; Kremmer, E.; Kato, H.; Akira, S.; Meyers, R.; Hacker, G.; Neuenhahn, M.; Busch, D.; Ruland, J.; Rothenfusser, S.; Prinz, M.; Hornung, V.; Endres, S.; Tuting, T.; Hartmann, G., 5'-triphosphate-siRNA: turning gene silencing and RIG-I activation against melanoma. Nature Medicine 2008, 14 (11), 1256-1263.
Robert Besch, H. P. T. H. D. S. G. H. C. B. V. H. S. E. T. R. S. R. G. H., Proapoptotic signaling induced by RIG-I and MDA-5 results in type I interferon-independent apoptosis in human melanoma cells. The Journal of clinical investigation 2009, 119 (8), 2399.
Matsushima-Miyagi, T.; Hatano, K.; Nomura, M.; Li-Wen, L.; Nishikawa, T.; Saga, K.; Shimbo, T.; Kaneda, Y., TRAIL and Noxa are selectively upregulated in prostate cancer cells downstream of the RIG-I/MAVS signaling pathway by nonreplicating Sendai virus particles. Clin Cancer Res 2012, 18 (22), 6271-83.
Schock, S. N.; Chandra, N. V.; Sun, Y.; Irie, T.; Kitagawa, Y.; Gotoh, B.; Coscoy, L.; Winoto, A., Induction of necroptotic cell death by viral activation of the RIG-I or STING pathway. Cell Death Differ 2017, 24 (4), 615-625.
Yuan, D.; Xia, M.; Meng, G.; Xu, C.; Song, Y.; Wei, J., Antiangiogenic efficacy of 5'-triphosphate siRNA combining VEGF silencing and RIG-I activation in NSCLCs. Oncotarget 2015, 6 (30), 29664-74.
Krieg, A. M., Therapeutic potential of Toll-like receptor 9 activation. Nature Reviews Drug Discovery 2006, 5 (6), 471-484.
Marq, J.- B.; Kolakofsky, D.; Garcin, D., Unpaired 5' ppp-Nucleotides, as Found in Arenavirus Double-stranded RNA Panhandles, Are Not Recognized by RIG-I. The Journal of Biological Chemistry 2010, 285 (24), 18208-18216.
Chan, Y. K.; Gack, M. U., Viral evasion of intracellular DNA and RNA sensing. Nat Rev Microbiol 2016, 14 (6), 360-73.
Alconcel, S. N. S.; Baas, A. S.; Maynard, H. D., FDA-approved poly(ethylene glycol)-protein conjugate drugs. Polymer Chemistry 2011, 2 (7), 1442-1448.
Zhang, Y.; Zhang, Y. F.; Bryant, J.; Charles, A.; Boado, R. J.; Pardridge, W. M., Intravenous RNA interference gene therapy targeting the human epidermal growth factor receptor prolongs survival in intracranial brain cancer. Clin Cancer Res 2004, 10 (11), 3667-77.
Gunasekaran, K.; Nguyen, T. H.; Maynard, H. D.; Davis, T. P.; Bulmus, V., Conjugation of siRNA with comb-type PEG enhances serum stability and gene silencing efficiency. Macromol Rapid Commun 2011, 32 (8), 654-9.
Kanasty, R.; Dorkin, J. R.; Vegas, A.; Anderson, D., Delivery materials for siRNA therapeutics. Nature Materials 2013, 12 (11), 967-977.
Oishi, M.; Nagasaki, Y.; Itaka, K.; Nishiyama, N.; Kataoka, K., Lactosylated Poly(ethylene glycol)-siRNA Conjugate through Acid-Labile β-Thiopropionate Linkage to Construct pH-Sensitive Polyion Complex Micelles Achieving Enhanced Gene Silencing in Hepatoma Cells. Journal of the American Chemical Society 2005, 127 (6), 1624-1625.
Jeong, J. H.; Mok, H.; Oh, Y.-K.; Park, T. G., siRNA Conjugate Delivery Systems. Bioconjugate Chemistry 2009, 20 (1), 5-14.
Schafer, F. Q.; Buettner, G. R., Redox environment of the cell as viewed through the redox state of the glutathione disulfide/glutathione couple. Free Radical Biology and Medicine 2001, 30 (11), 1191-1212.

(56) References Cited

OTHER PUBLICATIONS

Schlee, M.; Roth, A.; Hornung, V.; Hagmann, C. A.; Wimmenauer, V.; Barchet, W.; Coch, C.; Janke, M.; Mihailovic, A.; Wardle, G.; Juranek, S.; Kato, H.; Kawai, T.; Poeck, H.; Fitzgerald, K. A.; Takeuchi, O.; Akira, S.; Tuschl, T.; Latz, E.; Ludwig, J.; Hartmann, G., Recognition of 5' Triphosphate by RIG-I Helicase Requires Short Blunt Double-Stranded RNA as Contained in Panhandle of Negative-Strand Virus. Immunity 2009, 31 (1), 25-34.

Zitvogel, L.; Galluzzi, L.; Kepp, O.; Smyth, M. J.; Kroemer, G., Type I interferons in anticancer immunity. Nat Rev Immunol 2015, 15 (7), 405-14.

Gamcsik, M. P.; Kasibhatla, M. S.; Teeter, S. D.; Colvin, O. M., Glutathione levels in human tumors. Biomarkers 2012, 17 (8), 671-91.

Balendiran, G. K.; Dabur, R.; Fraser, D., The role of glutathione in cancer. Cell Biochemistry and Function 2004, 22 (6), 343-352.

MacEwan, S. R.; Callahan, D. J.; Chilkoti, A., Stimulus-responsive macromolecules and nanoparticles for cancer drug delivery. Nanomedicine (Lond) 2010, 5 (5), 793-806.

Zhu, L.; Torchilin, V. P., Stimulus-responsive nanopreparations for tumor targeting. Integr Biol (Camb) 2013, 5 (1), 96-107.

Zlatev, I.; Manoharan, M.; Vasseur, J. J.; Morvan, F., Solid-phase chemical synthesis of 5'-triphosphate DNA, RNA, and chemically modified oligonucleotides. Curr Protoc Nucleic Acid Chem 2012, Chapter 1, Unit 128.

Wincott, F.; DiRenzo, A.; Shaffer, C.; Grimm, S.; Tracz, D.; Workman, C.; Sweedler, D.; Gonzalez, C.; Scaringe, S.; Usman, N., Synthesis, deprotection, analysis and purification of RNA and ribozymes. Nucleic Acids Res 1995, 23 (14), 2677-84.

Tuschl, T.; Eckstein, F., Hammerhead ribozymes: importance of stem-loop II for activity. Proc Natl Acad Sci U S A 1993, 90 (15), 6991-4.

John C. Lindon, G. E. T., David Koppenaal, Encylopedia of Spectroscopy and Spectrometry. 3 ed.; 2016; p. 495-502.

Linehan, M.; Dickey, T.; Molinari, E.; Fitzgerald, M.; Potapova, O.; Iwasaki, A.; Pyle, A., A minimial RNA ligand for potent RIG-I activation in living mice. bioRxiv 2017, 178343.

Kohlway, A.; Luo, D.; Rawling, D.; Ding, S.; Pyle, A., Defining the functional determinants for RNA surveillance by RIG-I. EMBO reports 2013, 14 (9) 772-779.

Goldeck, M.; Tuschl, T.; Hartmann, G.; Ludwig, J., Efficient Solid-Phase Synthesis of pppRNA by Using Product-Specific Labeling. Angew. Chem. Int. Ed. 2014, 53, 4694-4698.

McCombs, J. R.; Owen, S. C., Antibody Drug Conjugates: Design and Selection of Linker, Payload and Conjugation Chemistry. The AAPS Journal 2015, 17 (2), 339-351.

Saneyoshi, H.; Yamamoto, Y.; Kondo, K.; Hiyoshi, Y.; Ono, A., Conjugatable and Bioreduction Cleavable Linker for the 5'-Functionalization of Oligonucleotides. J Org Chem 2017, 82 (3), 1796-1802.

Saravanakumar, G.; Kim, J.; Kim, W. J., Reactive-Oxygen-Species-Responsive Drug Delivery Systems: Promises and Challenges. Adv Sci (Weinh) 2017, 4 (1), 1600124.

Desnoyers, L. R.; Vasiljeva, O.; Richardson, J. H.; Yang, A.; Menendez, E. E.; Liang, T. W.; Wong, C.; Bessette, P. H.; Kamath, K.; Moore, S. J.; Sagert, J. G.; Hostetter, D. R.; Han, F.; Gee, J.; Flandez, J.; Markham, K.; Nguyen, M.; Krimm, M.; Wong, K. R.; Liu, S.; Daugherty, P. S.; West, J. W.; Lowman, H. B., Tumor-specific activation of an EGFR-targeting probody enhances therapeutic index. Sci Transl Med 2013, 5 (207), 207ra144.

Ryu, K. A.; McGonnigal, B.; Moore, T.; Kargupta, T.; Mancini, R. J.; Esser-Kahn, A. P., Light Guided In-vivo Activation of Innate Immune Cells with Photocaged TLR 2/6 Agonist. Sci Rep 2017, 7 (1), 8074.

Stutts, L.; Esser-Kahn, A. P., A Light-Controlled TLR4 Agonist and Selectable Activation of Cell Subpopulations. Chembiochem 2015, 16 (12), 1744-8.

Hang, C.; Zou, Y.; Zhong, Y.; Zhong, Z.; Meng, F., NIR and UV-responsive degradable hyaluronic acid nanogels for CD44-targeted and remotely triggered intracellular doxorubicin delivery. Colloids Surf B Biointerfaces 2017, 158 (1873-4367 (Electronic)), 547-555.

\* cited by examiner

PATTERN RECOGNITION RECEPTOR AGONIST PRODRUGS AND METHODS OF USE THEREOF

RELATED APPLICATIONS

This application is a national stage application, filed under 35 U.S.C. § 371, of International Patent Application No. PCT/US2019/012929, filed Jan. 9, 2019, which claims the benefit of U.S. Provisional Application Ser. No. 62/615,370, filed Jan. 9, 2018, the entire disclosures of which are incorporated herein by this reference.

GOVERNMENT INTEREST

This invention was made with government support under grant numbers T32DK101003 and 5R21AI121626 awarded by the National Institutes of Health (NIH), grant number W81XWH-16-1-0063 awarded by the Department of Defense (DOD) Congressionally Directed Medical Research Programs (CDMRP), and grant number CBET-1554623 awarded by the National Science Foundation (NSF). The government has certain rights in the invention.

SEQUENCE LISTING

The instant application contains a Sequence Listing which has been submitted in ASCII format via EFS-Web and is hereby incorporated by reference in its entirety. The ASCII copy of the Sequence Listing, which was created on Jan. 8, 2019, is named 11672N-18075W.txt and is 1 kilobyte in size.

TECHNICAL FIELD

The presently-disclosed subject matter relates to pattern recognition receptor (PRR) agonist prodrugs and methods of use thereof. In particular, the presently-disclosed subject matter relates to nucleic acid PRR agonists with macromolecules conjugated thereto and methods of use thereof.

BACKGROUND

The innate immune system plays a critical role in defense against pathogen infection, immune recognition of tumors, tissue repair and regeneration, and the pathogenesis of autoimmunity. Accordingly, there has been considerable interest in therapeutic strategies that modulate innate immune signaling pathways, including activation of the innate immune system as a strategy to combat cancer or improve the efficacy of vaccines. Upon microbial infection, tissue damage, or aberrant cellular behavior (e.g., tumor growth), the innate immune system initiates and coordinates a localized inflammatory response that typically restrains systemic inflammation and resultant toxicity and pathology. By contrast, administration of many molecular activators of the innate immune system results in systemic biodistribution and inflammation that limits the therapeutic window and/or restricts use to certain applications or administration routes (e.g., topical, intratumoral).

Pattern recognition receptors (PRRs) recognize specific molecular patterns associated with pathogen invasion to trigger an inflammatory response that is critical to mounting an appropriate immune response to clear the infection. A diversity of nucleic acid PRR agonists (e.g., CpG ODN, poly(I:C)) have been widely explored to activate innate immunity for applications in cancer immunotherapy and vaccine adjuvants. One important PRR involved in the detection of viruses is retinoic acid-inducible gene I (RIG-I, also known as DDX58), which resides in the cytosol and recognizes short, double-stranded RNA that contains a tri-phosphate group at the 5' end (pppRNA). Activation of RIG-I triggers a multifaceted anti-viral innate immune response that shares significant homology with responses that are associated with productive anti-tumor immunity (e.g., type I interferons, T cell chemokines). Additionally, activation of RIG-I in cancer cells has been shown to increase their immunogenicity as well as induce immunogenic cell death. Hence, agonists of the RIG-I pathway have recently emerged as a promising class of antiviral agents, vaccine adjuvants, and cancer immunotherapeutics, and are currently being evaluated in a clinical trial (NCT03065023).

However, unlike many other PRRs, which are expressed primarily in hematopoietic cells and often restricted to specific subsets of immune cells, RIG-I is present in the cytosol of virtually all cell types. Due to this ubiquity of RIG-I expression, the systemic administration of RIG-I agonists risks induction of systemic inflammation. Additionally, the risk for induction of system inflammation may carry with it possible dose-limiting toxicities.

Accordingly, there is a need for articles and methods for selective RIG-I pathway activation.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a selective pattern recognition receptor (PRR) agonist, comprising a nucleic acid agonist and a macromolecule conjugated to the nucleic acid agonist. In some embodiments, the nucleic acid agonist includes a nucleic acid duplex having at least two phosphoryl groups attached to a 5' end thereof. In one embodiment, the nucleic acid duplex comprises a double stranded nucleic acid molecule. In one embodiment, the nucleic acid duplex comprises a single-stranded nucleic acid molecule. In another embodiment, the single-stranded nucleic acid molecule comprises a hairpin loop RNA molecule. In one embodiment, the at least two phosphoryl groups are selected from the group consisting of a diphosphate group and a triphosphate group.

In some embodiments, the macromolecule has a molecular weight of at least 550 Da. In some embodiments, the selective PRR agonist further comprises an environmentally selective linker conjugating the macromolecule to the nucleic acid agonist. In one embodiment, the environmentally selective linker is selected from the group consisting of reactive oxygen species (ROS) sensitive linking agents, pH sensitive linking agents, redox sensitive linking agents, enzymatically cleavable linking agents, light sensitive linking agents, and combinations thereof. In another embodiment, the redox sensitive linking agents are selected from the group consisting of glutathione sensitive linkers, nitroreductase/NADH sensitive linkers, and combinations thereof. In another embodiment, the pH sensitive linking agents are selected from the group consisting of hydrazone, silyl ethers, other low pH sensitive linking agents, and combinations thereof. In another embodiment, the enzymatically cleavable linking agents are selected from the group consisting of matrix metalloproteinases, dipeptide/p-aminobenzyl alcohol systems, lysosomal, beta-glucuronidase, intracellular esterases, and combinations thereof.

In some embodiments, the macromolecule is conjugated to a 3' end of the nucleic acid duplex, the 3' end that the macromolecule is conjugated to and the 5' end that the at least two phosphoryl groups are attached to being at a single terminus of the nucleic acid duplex. In one embodiment, the agonist is a retinoic acid-inducible gene I (RIG-I) agonist. In some embodiments, the macromolecule is conjugated to a phosphoryl group attached to the 5' end of the nucleic acid duplex. In some embodiments, removal of at least a portion of the macromolecule permits binding of the agonist to a PRR.

Also provided herein, in some embodiments, is a method of selectively activating a pattern recognition receptor (PRR), the method comprising administering a selective PRR agonist to a subject; and cleaving at least a portion of the macromolecule conjugated to the nucleic acid duplex; wherein the cleaving of at least a portion of the macromolecule permits the agonist to bind a PRR. In some embodiments, the method further comprises an environmentally selective linker conjugating the macromolecule to the nucleic acid agonist. In some embodiments, the cleaving step comprises passively or actively subjecting the selective PRR agonist to an environmental stimulus corresponding to the environmentally selective linker. In some embodiments, the method further comprises a carrier system attached to the agonist.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein.

Figure 1:
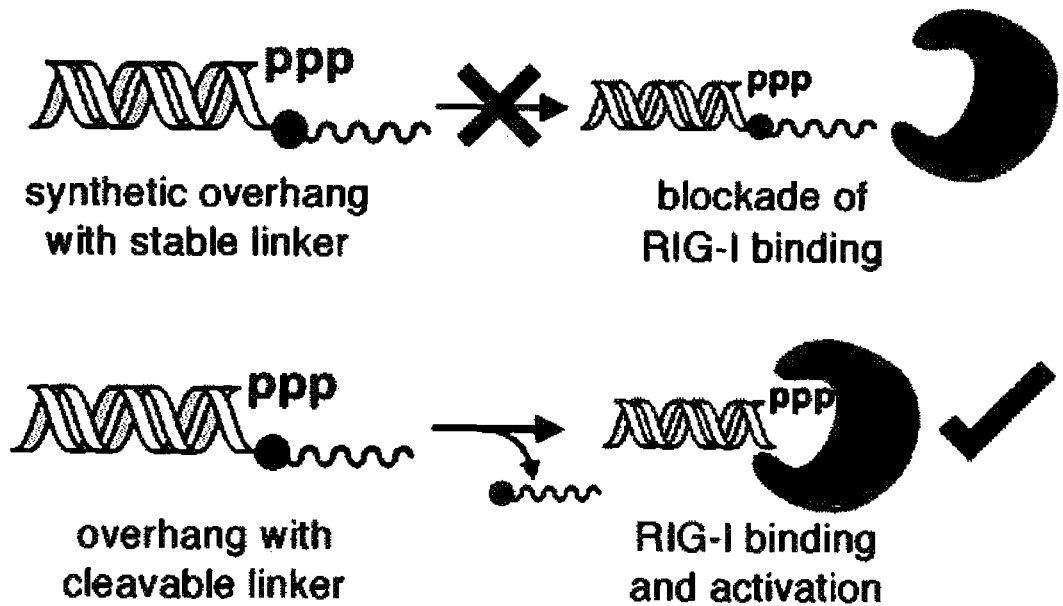
FIG. 1 shows a schematic illustration depicting the use of synthetic polymer overhangs to block activity of 5'ppp-RNA agonists of RIG-I, and that activity can be restored in response to environmental stimuli if synthetic overhangs are conjugated via a cleavable linker.

FIG. 2 shows a schematic illustration depicting the synthesis of PEG-pppRNA conjugates according to an embodiment of the disclosure.

FIGS. 3A-C show images depicting characterization of PEG-pppRNA conjugates. (A) Agarose gel electrophoresis demonstrating reduced migration distance with increased overhang molecular weight. UC=unconjugated pppRNA. PEG molecular weight and linker chemistry of PEG-pppRNA conjugates indicated above each lane. (B) Unconjugated pppRNA (left) and 550-mal-pppRNA (right) after 2% agarose gel electrophoresis at 148 V for 75 min. (C) Agarose gel electrophoresis of unconjugated cRNA (UC) and cRNA conjugates with $PEG_{5k}$ overhangs and indicated linker chemistry. Conjugates incubated with glutathione are indicated with '+GSH.'

FIG. 4 shows a graph illustrating dose-response curves comparing normalized Interferon Regulatory Factor (IRF) response in A549-Dual reporter cells elicited by unmodified pppRNA without a thiol group (unmodified), unconjugated, thiol-containing pppRNA (unconjugated), and vehicle (Lipofectamine 2000) control.

FIGS. 5A-D show graphs illustrating the effect of PEG synthetic overhang molecular weight, linker cleavability, and conjugation site on ppp-RNA mediated activation of interferon regulatory factor (IRF) pathway. (A) Dose-response curve comparing the response to unconjugated pppRNA and those conjugated with maleimide-linked PEG-pppRNA at indicated molecular weights. (B) Dose-response curves comparing the response to unconjugated pppRNA and pppRNA conjugated to $PEG_{5k}$-mal on the side opposite the 5'ppp motif (C) Dose-response curve comparing the response to unconjugated pppRNA and those conjugated to $PEG_{5k}$ overhangs with indicated linker chemistry. (D) Bar graph comparing the EC50 of all groups tested. (o) denotes conjugation on the side opposite the 5'ppp motif*p=0.0003 and **p<0.0001 by one-way ANOVA with Tukey's test.

FIG. 6 shows a graph comparing relative IRF response in A549-Dual reporter cells to cRNA lacking the 5'ppp group, pppRNA, and 5 kDa PEG-cRNA conjugates of indicated linker chemistry. Cells treated at 20 nM concentrations of indicated treatment.

FIG. 7 shows a graph illustrating concentration of hIFN-β1 secreted by A549-Dual cells treated with $PEG_{5k}$-pppRNA conjugates (at 20 nM RNA) with indicated linker chemistry.  p<0.01**p<0.0001 one-way ANOVA with Tukey's test.

FIG. 8 shows a schematic illustrating selective immune response in the presence of an appropriate stimulus, according to an embodiment of the disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

Definitions

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments±50%, in some embodiments ±40%, in some embodiments±30%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that unless stated otherwise each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

All combinations of method or process steps as used herein can be performed in any order, unless otherwise specified or clearly implied to the contrary by the context in which the referenced combination is made.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter relates to pattern recognition receptor (PRR) agonists and methods of use thereof. In some embodiments, the PRR agonist includes a selective nucleic acid agonist including at least one macromolecule conjugated thereto. Suitable nucleic acid agonists include any molecularly-defined nucleic acid agonist of a PRR. As will be appreciated by those skilled in the art, the specific PRR of interest will determine the nucleic acid agonist that is selected.

In some embodiments, the nucleic acid agonist includes a phosphorylated nucleic acid duplex. As used herein, the term "phosphorylated nucleic acid duplex" refers to any molecule including ribonucleic acid (RNA) and/or deoxyribonucleic acid (DNA) base pairing between complementary nucleotide sequences in the same or separate nucleic acid strands, and at least two phosphoryl groups (e.g., diphosphate or triphosphate) at a 5' end of at least one strand. Various PRRs, such as, but not limited to, retinoic acid-inducible gene I (RIG-I), recognize the phosphoryl groups attached to these phosphorylated nucleic acid duplexes, resulting in binding thereto.

In one embodiment, the phosphorylated nucleic acid duplex includes a double-stranded nucleic acid molecule with base pairing between separate, complementary strands. In another embodiment, the phosphorylated nucleic acid duplex includes a double-stranded RNA molecule, which may be comprised entirely of RNA bases or a combination of RNA bases and at least one DNA base. In a further embodiment, one or more of the RNA and/or DNA bases may be modified, such as, for example, by including a phosphothioate linkage. These double-stranded nucleic acid molecules include at least 8 base pairs, at least 10 base pairs, between 10 and 1000 base pairs, between 10 and 750 base pairs, between 10 and 500 base pairs, between 10 and 250 base pairs, between 10 and 100 base pairs, between 10 and 50 base pairs, between 10 and 40 base pairs, between 10 and 30 base pairs, between 10 and 20 base pairs, between 10 and 14 base pairs, 8 base pairs, 10 base pairs, 12 base pairs, 14 base pairs, 16 base pairs, 18 base pairs, 20 base pairs, 22 base pairs, 24 base pairs, 26 base pairs, 28 base pairs, 30 base pairs, more than 30 base pairs, or any combination, sub-combination, range, or sub-range thereof. In some embodiments, each double-stranded nucleic acid molecule includes two termini, each terminus including the 5' end of one strand and the 3' end of the other, complementary strand. In such embodiments, the 5' end of at least one strand is phosphorylated with a diphosphate or triphosphate group.

In an alternate embodiment, the nucleic acid duplex includes a single-stranded nucleic acid molecule with base pairing between complementary regions within the same strand. These single-stranded nucleic acid duplexes have a single terminus including both the 5' and 3' end of the single strand. In such embodiments, the 5' end of the single strand is phosphorylated with a diphosphate or triphosphate group. In one embodiment, the single-stranded nucleic acid molecule includes at least 8 base pairs, at least 10 base pairs, between 8 and 100 base pairs, between 8 and 80 base pairs, between 8 and 60 base pairs, between 8 and 50 base pairs, between 8 and 40 base pairs, between 8 and 30 base pairs, between 10 and 30 base pairs, between 10 and 20 base pairs, between 10 and 14 base pairs, 8 base pairs, 10 base pairs, 12 base pairs, 14 base pairs, 16 base pairs, 18 base pairs, 20 base pairs, 22 base pairs, 24 base pairs, 26 base pairs, 28 base pairs, 30 base pairs, more than 30 base pairs, or any combination, sub-combination, range, or sub-range thereof. In another embodiment, the single-stranded nucleic acid duplex includes, but is not limited to, a stem-loop or hairpin loop RNA. In a further embodiment, the stem-loop RNA includes an RNA tetraloop opposite the single terminus. This RNA tetraloop stabilizes the stem-loop RNA molecule and/or blocks protein binding. Although discussed above in terms of an RNA molecule, as will be appreciated by those skilled in the art, these molecules are not limited solely to RNA bases and may include at least one DNA base.

Although discussed herein primarily with regard to phosphorylated nucleic acid duplexes, as will be appreciated by those skilled in the art, the disclosure is not so limited and may include any other suitable nucleic acid agonist for the PRR of interest. In some embodiments, the nucleic acid agonist includes a specific nucleic acid ligand for the PRR and/or an immunostimulatory oligonucleotide. For example, the nucleic acid agonist may include a single stranded oligonucleotide, such as CpG ODN (TLR-9 ligand); double-stranded DNA, such as a cGAS ligand; single stranded RNA, such as TLR-7/8 ligands; any other suitable nucleic acid agonist; or a combination thereof.

Turning to the at least one macromolecule conjugated to each of the nucleic acid agonists disclosed herein, in some embodiments, the macromolecule includes any molecule having a molecular weight of at least 300 Da, at least 350 Da, at least 400 Da, at least 450 Da, at least 500 Da, at least 550 Da, between about 300 Da and about 10,000 Da, between about 300 Da and about 7,500 Da, between about 300 Da and about 5,000 Da, between about 300 Da and about 4,000 Da, between about 300 Da and about 3,000 Da, between about 300 Da and about 2,000 Da, between about 300 Da and about 1000 Da, between about 400 Da and about 1000 Da, between about 500 Da and about 1000 Da, between about 550 and about 1000 Da, greater than 1000 Da, or any combination, sub-combination, range, or sub-range thereof. In some embodiments, the macromolecule includes any covalently attached molecule that inhibits PRR binding or activity by at least 75% through steric hindrance. In some embodiments, the macromolecule includes a polymer, a peptide, a lipid, a nucleic acid molecule, a carbohydrate, any other suitable macromolecule, or a combination thereof. Suitable polymer macromolecules include, but are not limited to, poly(ethylene glycol), polyethers, polyesters, polycarbonates, polyvinyls, polyamino acids, polysulfobetaines, carboxybetaines, or combinations thereof. Additionally or alternatively, the polymer macromolecules may include pH-responsive and/or endosome destabilizing polymers.

In some embodiments, at least one of the macromolecules disclosed herein is conjugated to a 3' end of the nucleic acid duplex at the same terminus as the phosphorylated 5' end. For example, in one embodiment, the 5' end of one strand of a double stranded RNA duplex is phosphorylated and a macromolecule is conjugated to the 3' end of the complementary strand, such that the phosphate groups and the macromolecule are on separate strands at the same terminus. In another embodiment, the double stranded RNA duplex includes at least two phosphate groups at each 5' end and a macromolecule conjugated to at least one complementary 3' end. In a further embodiment, each strand of the double stranded RNA duplex includes at least two phosphate groups at the 5' end and a macromolecule conjugated to the complementary 3' end. Turning to embodiments where there is only one terminus, such as the single-stranded duplex, the 5' end of the single terminus is phosphorylated and the macromolecule is conjugated to the 3' end thereof. As used herein, the phrase "conjugated to a 3' end" refers to a macromolecule conjugated to the nucleic acid duplex at any nucleotide within 5 nucleotides of the 3' end thereof.

Additionally or alternatively, the macromolecule may be conjugated to the gamma phosphate of the phosphate group at the 5' end of the nucleic acid duplex. In one embodiment, the conjugation of the macromolecule to the gamma phosphate includes formation of a $P^{III}$-$P^{V}$ cyclic anhydride, followed by oxidation with tBuOOH and washing with anhydrous acetonitrile to form a solid-phase-bound RNA cyclotriphosphate, and then reaction with a macromolecule solution in acetonitrile. Although discussed above primarily with regard to conjugation of the macromolecule to a 3' end of a nucleic acid duplex, as will be appreciated by those skilled in the art, the disclosure is not so limited and includes the macromolecule conjugated to any other nucleic acid agonist disclosed herein in any position suitable for inhibiting binding to and/or activation of the associated PRR.

According to one or more of the embodiments disclosed herein, the macromolecule may be conjugated to the nucleic acid agonist through any suitable linking agent. In some embodiments, the linking agent is a cleavable and/or environmentally reactive linking agent, such as, but not limited to, reactive oxygen species (ROS) cleavable linking agents, reactive nitrogen species cleavable linking agents, pH cleavable linking agents, redox cleavable linking agents, enzymatically cleavable linking agents, light sensitive linking agents, temperature responsive linking agents, oxygen sensitive linking agents, reductase sensitive linking agents, or a combination thereof. For example, in one embodiment, redox sensitive linking agents include, but are not limited to, glutathione sensitive linkers (e.g., disulfide linkers), nitroreductase/NADH sensitive linkers, or a combination thereof. In another embodiment, the pH sensitive linking agent includes, but is not limited to, hydrazone, silyl ethers, other low pH sensitive linking agents, or a combination thereof. In a further embodiment, the enzymatically cleavable linking agents include, but are not limited to, matrix metalloproteinases, dipeptide/p-aminobenzyl alcohol systems (which are tunable for half-lives between 9 and 240 h), lysosomal, beta-glucuronidase, intracellular esterases, or a combination thereof.

Without wishing to be bound by theory, it is believed that conjugation of the macromolecule to the nucleic acid agonist inhibits binding of the agonist to the PRR through steric hindrance. By providing selective removal of at least a portion of the macromolecule, the nucleic acid agonists disclosed herein provide selective activation of the associated receptors, thus avoiding unwanted systemic activation. Accordingly, in some embodiments, such as where the macromolecule is conjugated through an environmentally sensitive linking agent, the nucleic acid agonists disclosed herein form a new class of nucleic acid prodrugs. For example, in one embodiment, upon removal of at least a portion of the macromolecule conjugated to a phosphorylated nucleic acid duplex, the RIG-I receptor recognizes the 5' phosphorylated duplex, regardless of nucleotide sequence, and triggers a response. While the portion of the macromolecule removed depends upon the specific macromolecule, nucleic acid agonist, and PRR, as used herein, the term "at least a portion of the macromolecule" refers to any portion which removal thereof restores at least 25% of the agonist activity. In some embodiments, this includes any portion that leaves behind a residual macromolecule and/or linker of less than 1000 Da. In some embodiments, this includes any portion that leaves behind a residual macromolecule and/or linker of less than 900 Da, less than 800 Da, less than 700 Da, less than 600 Da, less than 500 Da, less than 400 Da, less than 300 Da, less than 200 Da, or any combination, sub-combination, range, or sub-range thereof.

In some embodiments, these prodrugs are capable of activating the PRR pathway, such as the RIG-I pathway or any other suitable PRR pathway, in response to environmental stimuli that cleave at least a portion of the macromolecule from the nucleic acid agonist. In one embodiment, the environmental stimuli include any stimuli corresponding to the environmentally sensitive linker. As will be appreciated by those skilled in the art, the specific environmental stimuli will depend upon the specific linking agent attaching the macromolecule to the nucleic acid agonist, and the linker may be passively or actively exposed to the environmental stimuli. For example, the pH cleavable linking agents are cleaved when exposed to specific pH, which may be present in some environments but not in other. In another example, the light sensitive linking agents are cleaved when exposed to specific light waves, which may be applied to selected areas of a subject. Through the use of different linker chemistries and conjugation sites, the PRR agonists disclosed herein may form various bioconjugates and prodrugs based on the nucleic acid agonists disclosed herein, such as, but not limited to, agonist-antibody conjugates for tumor targeting and/or agonist-antigen conjugates for vaccination. Accordingly, in some embodiments, the prodrugs may be used as vaccine adjuvants, cancer immunotherapies, antiviral agents, or any other application where selective activation of the RIG-I pathway or any other suitable pathway is desired.

Also provided herein, in some embodiments, is a composition including the PRR agonist and a carrier system. The carrier system includes any suitable compound that improves physiochemical and/or pharmacokinetic properties of the PRR agonist when attached and/or linked to the nucleic acid agonist thereof. In some embodiments, the macromolecule forms the carrier system. Alternatively, in some embodiments, the carrier system is attached and/or linked to the nucleic acid agonist in addition to the macromolecule. Suitable carrier systems include, but are not limited to, polymeric compounds, liposomes, micelles, microspheres, nanoparticles, or a combination thereof. For example, suitable carrier systems include, but are not limited to, linear and branched cationic polymers, including both synthetic and naturally occurring polymers (e.g., chitosan, poly(L-lysine), polyethylenimine (PEI), (dimethylamino) ethyl methacrylate (DMAEMA), poly(beta-amino esters, and cell penetrating peptides); dendrimers, including cationic dendrimers for electrostatic complexation of RNA and dendrimer-RNA conjugates; DMAEMA-block-(DMAEMA-co-BMA-co-PAA) where BMA=butyl methacrylate and PAA=propyl acrylic acid; antibodies for generating antibody-duplex conjugates; poly(lactic-co-glycoolic acid) (PLGA) micro- and nanoparticles; lipid and lipidoid nanoparticles; or combinations thereof.

In one embodiment, the carrier system is attached and/or linked to the PRR agonist through a labile bridge. In another embodiment, the carrier system encapsulates the PRR agonist. In a further embodiment, the PRR agonist is electrostatically complexed with the carrier system. As will be appreciated by those skilled in the art, suitable carrier systems will depend upon the target site for nucleic acid agonist delivery/PRR activation.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

This Example describes the generation of a "synthetic overhang" by conjugating macromolecules to the 3' end of the complement strand to a 5' triphosphorylated RNA to block the immunostimulatory properties of the nucleic acid and overcome the risk of increased toxicity resulting from induction of systemic anti-viral innate immunity through systemic administration of RIG-I agonists. This Example also shows restoration of agonist activity in response to specific environmental stimuli when the synthetic overhang is linked to the RNA via a cleavable linker (FIG. 1).

To generate the synthetic overhang, monomethyl poly (ethylene glycol) (PEG) was conjugated to pppRNA. PEG was chosen as a synthetic overhang due to its to aqueous solubility, biocompatibility, and widespread use in clinically approved biomacromolecular therapeutics. Investigation of the effect of PEG molecular weight, conjugation site, and linker cleavability on the ability of PEG-pppRNA conjugates to activate the RIG-I pathway in vitro is also discussed below.

Materials and Methods

Materials

Methoxy-poly(ethylene glycol) functionalized with ortho-pyridinyl disulfide (PEG-OPSS, $M_n$ 5000), and methoxy-poly(ethylene glycol) functionalized with maleimide at varying molecular weights (PEG-MAL, $M_n$ 550, 1000, 2000, and 5000) were obtained from Creative PEGWorks (Chapel Hill, NC). Oligonucleotide synthesis reagents were purchased from BioAutomation (Irving, TX). Dithiothreitol (DTT), reduced glutathione (GSH), chromatography-grade methanol, and oligonucleotide triphosphorylation and deprotection reagents were obtained from Sigma-Aldrich (St. Louis, MO). Heat-inactivated fetal bovine serum (HI-FBS), phosphate-buffered saline (PBS), penicillin/streptomycin solution, and Roswell Park Memorial Institute 1640 medium (RPMI) and Dulbecco's Modified Eagle Medium (DMEM) were procured from Gibco (Grand Island, NY). 0.5 M disodium N,N,N',N'-ethylenediamine tetraacetic acid (EDTA) solution was purchased from Corning (Corning, NY). Lipofectamine 2000 was acquired from Invitrogen (Carlsbad, CA). Chromatography-grade triethylamine and glacial acetic acid were obtained from Fisher Scientific (Hampton, NH). All other reagents were analytical grade.

Chemically Modified RNAs

5'-triphosphorylated sense strand RNA (sequence: 5'-CGU AAA UCG CGU AUA CGC CUA U-3') (SEQ ID NO: 1) was synthesized on a MerMade 12 automated RNA-DNA synthesizer (BioAutomation) as described previously. Base deprotection was carried out using ammonium hydroxide-methylamine solution (AMA) as described previously with minor modifications. The oligonucleotide on polymer support was transferred into a glass vial with 4 mL of AMA solution (1:1 (v/w) mixture of 30% ammonium hydroxide and 40% methylamine) before incubation at 65° C. for 10 min to remove the oligonucleotide from the support and to remove protecting groups from bases and phosphates. After cooling on ice for 10 min, the supernatant was transferred to a clean vial. The support was washed with 500 μL of acetonitrile:water:ethanol mixture (1:1:3 v/w) and the wash was combined with the supernatant. The resulting mixture was evaporated to dryness using a SpeedVac to yield a pellet, which was rewetted with 500 μL of ethanol and evaporated to dryness again.

Deprotection of the 2'—OH groups was carried out as described previously with minor modifications. The pellet was dissolved in 500 μL of a 1M solution of tetrabutylammonium fluoride (TBAF) in tetrahydrofuran and incubated at room temperature for at least 24 h with gentle shaking. 500 μL of sodium acetate (pH 6.0) was then added and the mixture before being evaporated to a volume of ~500 μL. The resulting mixture was extracted 3 times with ethyl acetate to remove TBAF, and the deprotected oligonucleotide was precipitated with 1.6 mL of ethanol and purified on a 16% denaturing polyacrylamide gel. The oligonucleotide was visualized by UV-shadowing, excised from the gel and eluted by incubation of gel slices in a solution containing 10 mM MOPS (pH 6.0), 1 mM EDTA, and 300 mM NaCl at 4° C. overnight with gentle shaking.

3'- and 5'-disulfide-modified antisense strand RNA (sequence: 5'-AUA GGC GUA UUA UAC GCG AUU AAC G-3') (SEQ ID NO: 2), as well as 5'-non-phosphorylated sense strand and unmodified antisense strand RNAs were purchased from Integrated DNA Technologies (Coralville, IA). 3' or 5'-disulfide modified antisense RNA was annealed to 5'-triphosphorylated sense RNA or 5'-unphosphorylated control sense RNA to yield double-stranded RNA (pppRNA and cRNA, respectively) by incubating equimolar concentrations of each strand in 100 mM NaCl at 90° C. and slowly reducing the temperature to room temperature over 45 min.

Synthesis of PEG-RNA Conjugates

To synthesize PEG-RNA conjugates, thiolated double-stranded RNA in the form of a protected disulfide was reduced by adding 1.2 mg of dithiothreitol (DTT, 80 µmol) to a solution containing 125 µg of RNA (pppRNA or RNA, 7.75 nmol) suspended in water. After incubating for 30 min at room temperature, the excess DTT and other small-molecule reaction byproducts were removed by buffer exchange into a solution containing PBS, 10 mM EDTA, and 0.02% sodium azide (w/v) with a size exclusion chromatography column (Zeba™ Spin Desalting Columns, Thermo Scientific, Waltham, MA). 15 µg of the desalted, thiolated RNA (950 pmol) was then combined with 1.2 mg of functionalized mPEG (mPEG-OPSS or mPEG-MAL, 240 nmol) and was allowed to react overnight at room temperature. Aliquots of the resulting products were then taken for agarose gel analysis, and the remainder was buffer exchanged into 50 mM triethylammonium acetate, pH 7.5 by centrifugal diafiltration (Amicon Ultra centrifugal filters, 10 kDa MWCO, EMD Millipore, Burlington, MA) and analyzed by ion-paired reverse-phase HPLC on a Clarity C18 column (50 mm×4.6 mm, 5 µm, Phenomenex, Torrance, CA) equipped with a dual-channel UV detector at 260 and 280 nm (Waters, Milford, MA) and utilizing the following method: buffer A, 50 mM triethylammonium acetate, pH 7.5; buffer B, methanol; gradient, 5% to 100% buffer B in 50 min after 5 min dwell time; flow rate 1 mL/min; ambient column temperature. The appropriate HPLC fractions were pooled (Table 1), then concentrated and buffer exchanged into ultrapure water by centrifugal diafiltration (3 kDa MWCO).

TABLE 1

Times during which elute was collected during HPLC for each sample.

| Sample | Collection Begin (min) | Collection End (min) |
|---|---|---|
| unconjugated pppRNA | 15.4 | 19.8 |
| pppRNA + 550-mal | 19 | 25 |
| pppRNA + 1k-mal | 22 | 26 |
| pppRNA + 2k-mal | 25 | 31 |
| pppRNA + 5k-mal | 33 | 37 |
| pppRNA + 5k-ss | 33 | 37 |
| pppRNA + 5k-mal (opposite side) | 33 | 37 |

Characterization of PEG-RNA Conjugates

To verify PEG conjugation and product purity, the HPLC purified products were imaged after agarose gel electrophoresis in Tris-borate-EDTA buffer with 2% agarose at 148 V for 30 or 75 min. Area-under-the-curve absorbance ratios were evaluated during HPLC analysis to estimate conjugation efficiency. This analysis was performed using absorbance values at 280 nm, as disulfide bonds absorb weakly between 250 and 270 nm. To verify the cleavability and non-cleavability of the disulfide and maleimide linkages (respectively), the reaction products were incubated in 10 mM GSH at 37° C. for 24 h before visualization via agarose gel electrophoresis and analysis as previously described.

Cell Culture

All cell culture assays were performed using A549 Dual Reporter cells (Invivogen). A549s were cultured in DMEM supplemented with 4.5 g/L glucose, 10% HI-FBS, 2 mM L-glutamine, 100 units/mL penicillin, and 100 µg/mL streptomycin at 37° C. in a humidified atmosphere containing 5% $CO_2$. 5,000 cells were plated into 96-well plates and transfected in quadruplicate with Lipofectamine 2000 transfection reagent according to the manufacturer's instructions with 20 nM concentrations of conjugates. Dose sweeps started at 20 nM, followed by serial 2-fold dilutions down to 156.25 pM. IFN-β concentrations in cell supernatant were determined using a Lumikine hIFN-β kit (Invivogen) according to the manufacturer's instructions. Luminescent reporter assays were performed using QUANTI-Luc (Invivogen) according to the manufacturer's instructions. Measurements were taken using a Synergy H1 microplate reader (BioTek, Winooski, VT). All measurements were normalized after baselining to the average value of the PBS-treated negative control group.

Results and Discussion

Figure 2:
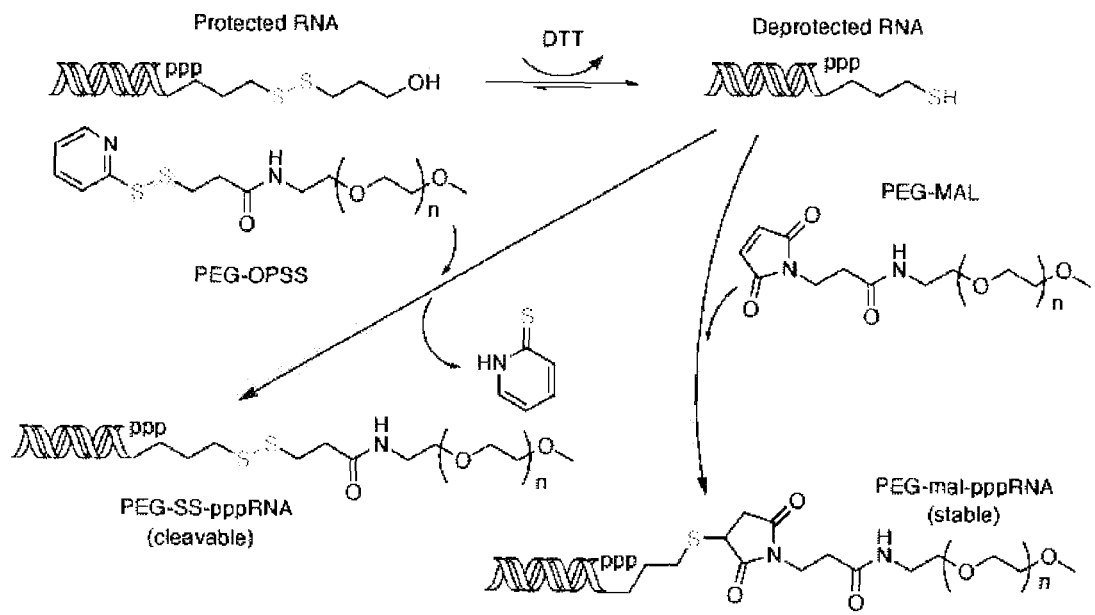

The synthesis scheme used to conjugate monofunctionalized PEG to pppRNA is depicted in FIG. 2. In summary, the n-hydroxypropyl disulfide protecting group was removed by reduction with excess dithiothreitol (DTT) to yield double stranded oligonucleotides with a free thiol group at the 3' end of strand complementary to 5'ppp-containing strand. Thiolated pppRNAs were subsequently reacted with ortho-pyridyl disulfide- or maleimide-functionalized PEG of various molecular weight (MW) to yield pppRNA conjugates containing either a reducible disulfide linkage ($PEG_{MW}$-SS-pppRNA) or a stable thioether linkage ($PEG_{MW}$-mal-pppRNA).

Figure 3A:
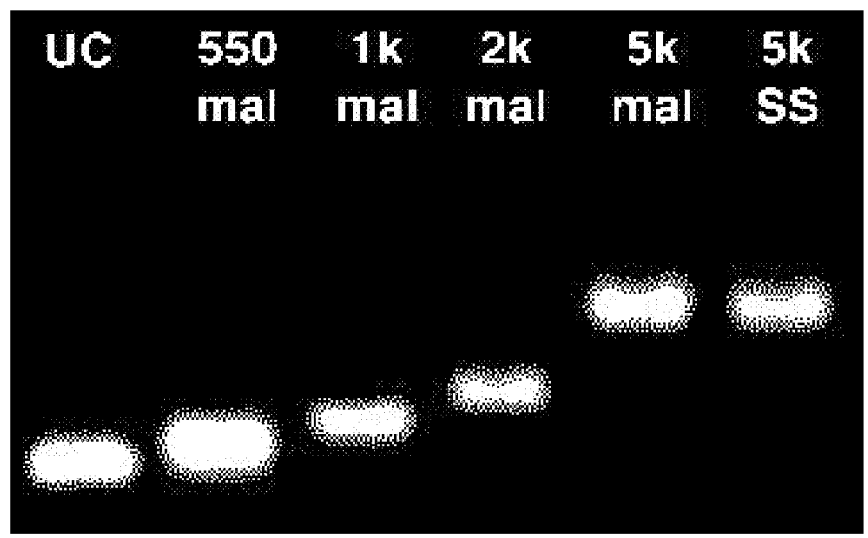
Figure 3B:
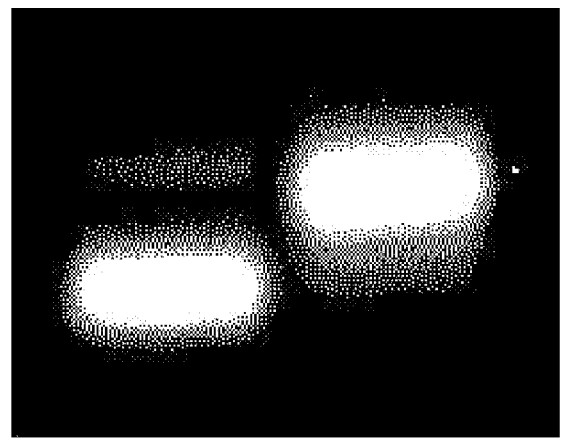
Figure 3C:
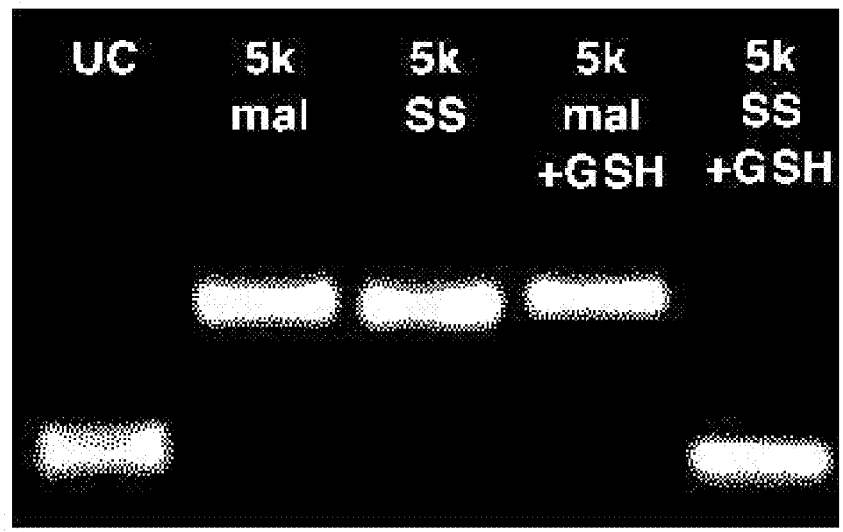

Conjugation efficiency was determined by area-under-the-curve integration during HPLC purification (Table 2). Agarose gel electrophoresis depicted shifts in RNA migration distances that were consistent with the molecular weight of the conjugated PEG (FIG. 3A). Additional gel electrophoresis was performed to further confirm the absence of unconjugated pppRNA in the HPLC-purified $PEG_{550}$-mal-pppRNA conjugate (FIG. 3B). These procedures were repeated with control RNA lacking the 5'ppp moiety (cRNA) to produce negative control conjugates (Table 3). To evaluate whether synthetic overhangs could be removed when linked via a reducible disulfide bond but not a thioester linkage, cRNA conjugates synthesized with 5 kDa PEG were incubated with cytosolic levels (10 mM) of glutathione prior to electrophoresis. cRNA was completely liberated from disulfide-linked overhangs, whereas conjugates with stable maleimide linkers remained intact (FIG. 3C), demonstrating that cleavable linkers can be used for stimuli-responsive removal of synthetic overhangs.

TABLE 2

Conjugation efficiencies of PEG-pppRNA conjugates used in this study.

| Sample | % Conjugation |
|---|---|
| pppRNA + 550-mal | 86.6 |
| pppRNA + 1k-mal | 37.3 |
| pppRNA + 2k-mal | ≥98 |
| pppRNA + 5k-mal | ≥98 |
| pppRNA + 5k-ss | 63.1 |
| pppRNA + 5k-mal (opposite side) | 95.3 |

TABLE 3

Conjugation efficiencies of PEG-cRNA conjugates used in this study.

| Sample | % Conjugation |
| --- | --- |
| cRNA + 5k-mal | ≥98 |
| cRNA + 5k-ss | 59.5 |

Figure 4:
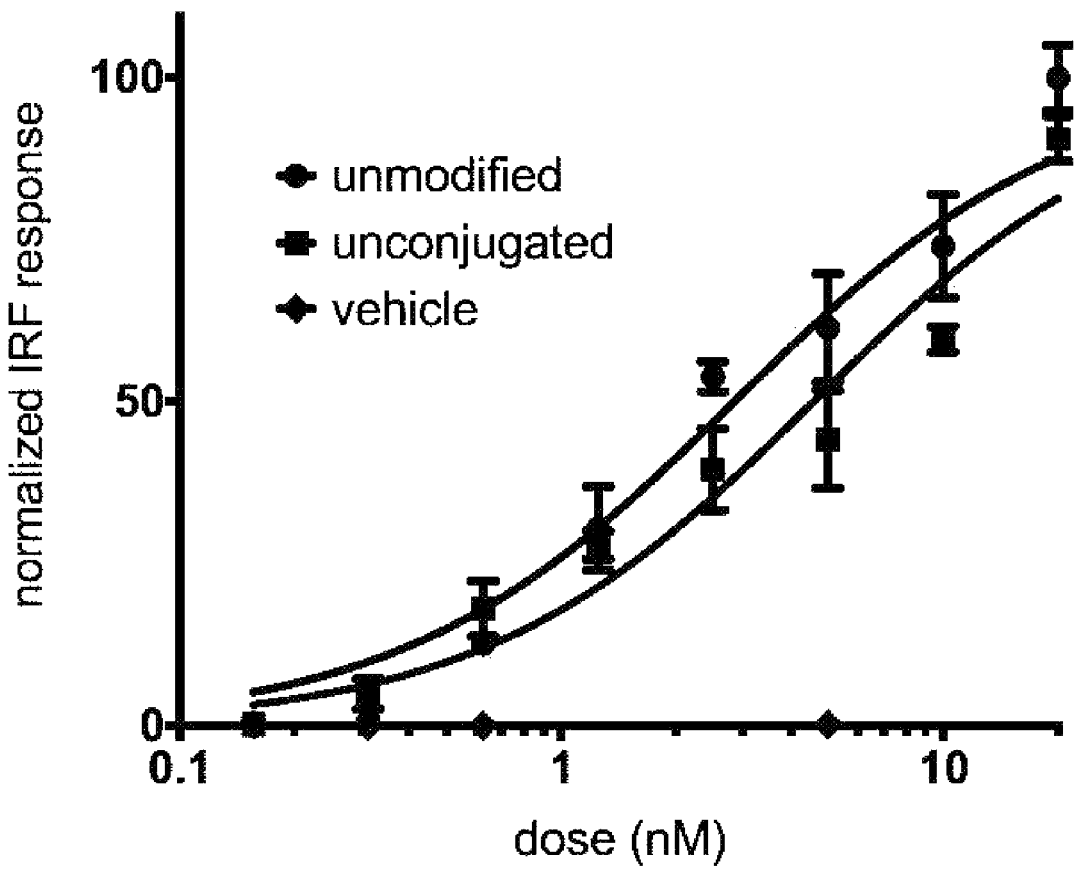
Figure 5A:
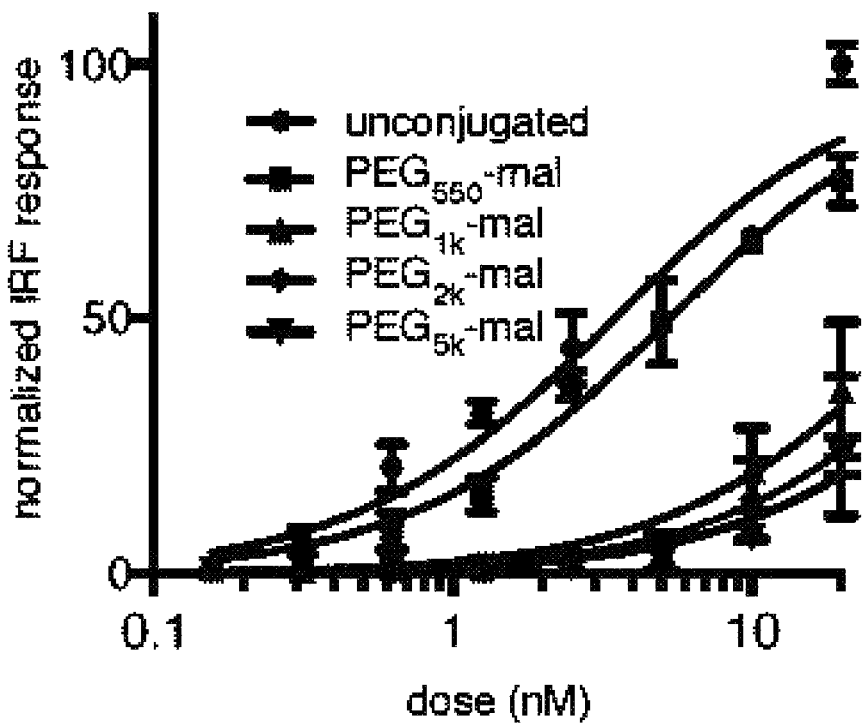
Figure 6:
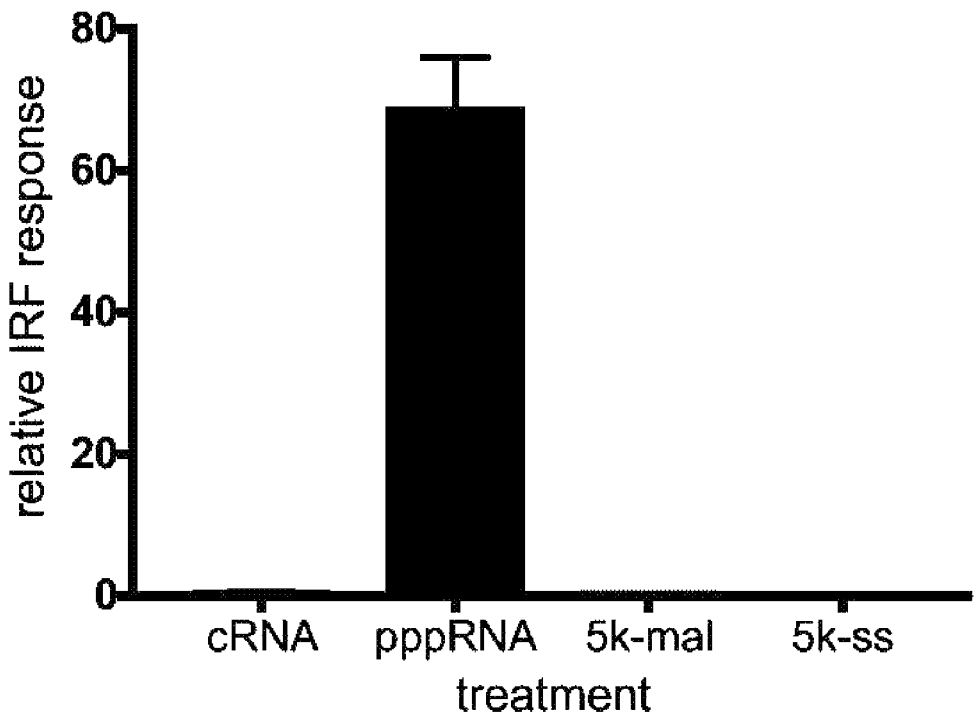
Figure 7:
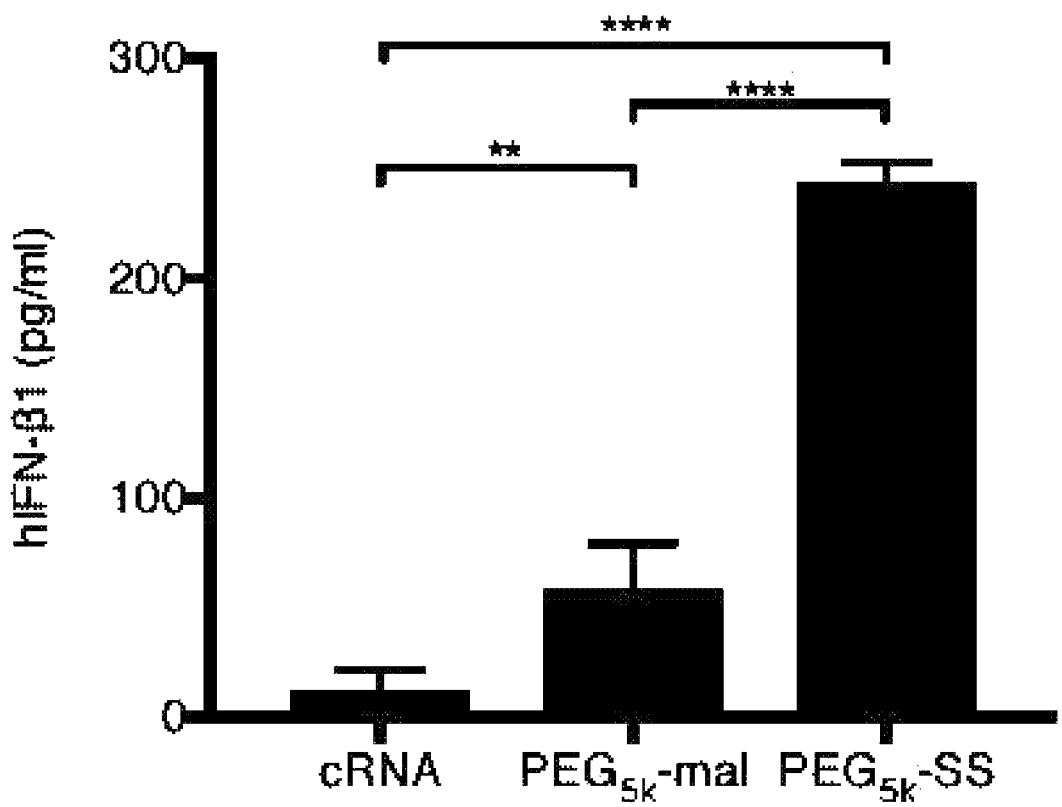
Figure 8:
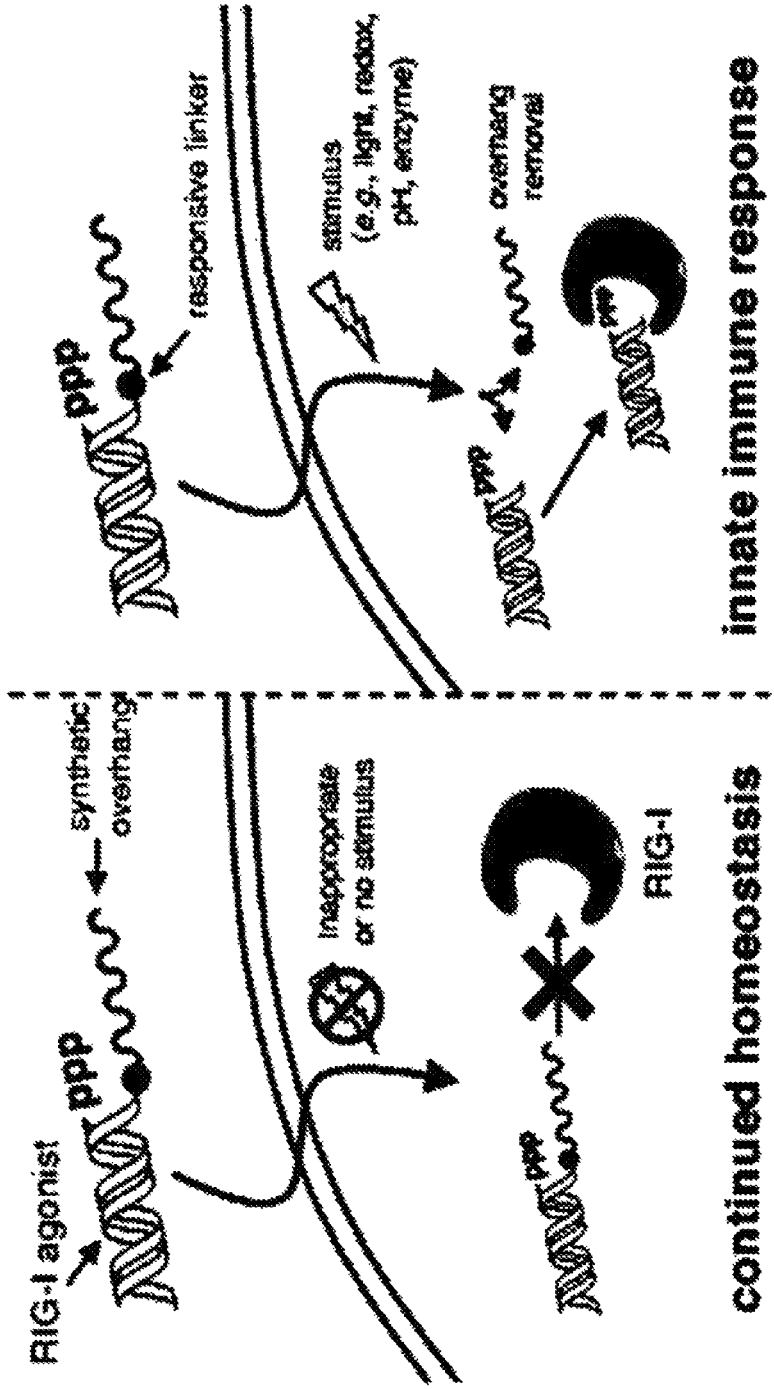

To evaluate the effect of synthetic overhangs on RIG-I activation, PEG-pppRNA conjugates of indicated overhang molecular weight and linker chemistry were complexed with a lipid-based transfection reagent (Lipofectamine 2000) to mediate cytosolic delivery, and incubated with human lung carcinoma cells with an interferon regulatory factor (IRF) pathway reporter gene (A549-Dual). The effect of introducing a propanthiol group on the 3' end of the complement strand was first evaluated by comparing IRF pathway activation to unmodified pppRNA. A significant effect on ligand activity was not observed (FIG. 4). The effect of PEG overhang molecular weight was then examined using maleimide-linked PEG overhangs of 550 Da, 1 kDa, 2 kDa, and 5 kDa. Interestingly, conjugation of 550 Da PEG had minimal impact on ligand activity, whereas all larger molecular weights (1, 2, 5 kDa) dramatically inhibited ligand activity to approximately the same extent, suggesting a minimum molecular weight threshold for successful ablation of RIG-I activation (FIG. 5A). This is conceptually consistent with the ability of RIG-I to recognize pppRNA with short (i.e., 1-3 nucleotides) 3' RNA overhangs, albeit at the expense of activity. Additionally, $PEG_{5k}$-cRNA conjugates were delivered to cells to evaluate the degree of immunogenicity present solely due to the presence of the synthetic overhang and linker chemistry. As expected, control RNA without the 5'ppp moiety (cRNA) lacked immunostimulatory activity, which was not effected by conjugation of 5 kDa PEG (FIG. 6).

Figure 5B:
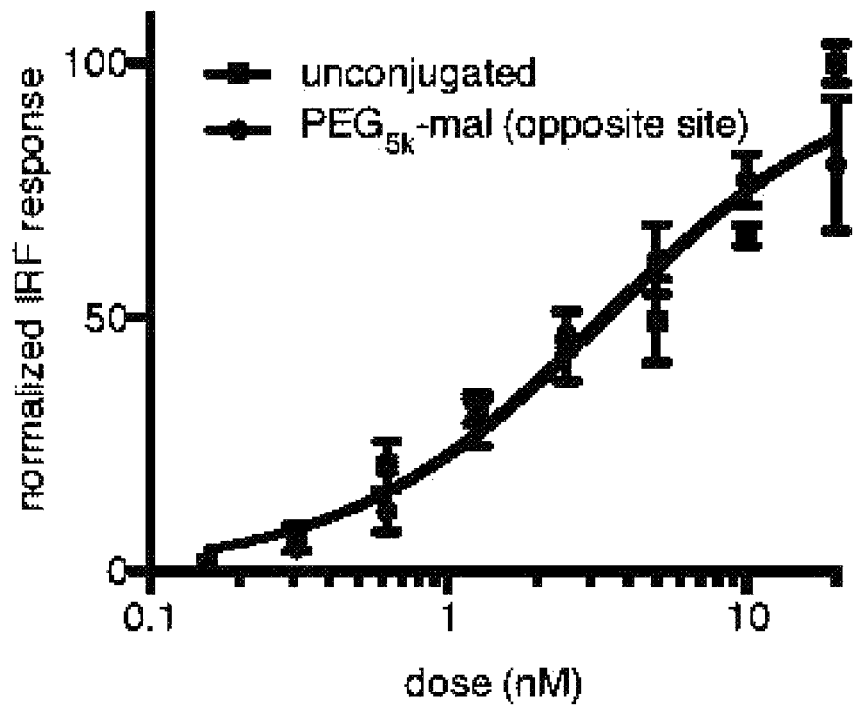
Figure 5C:
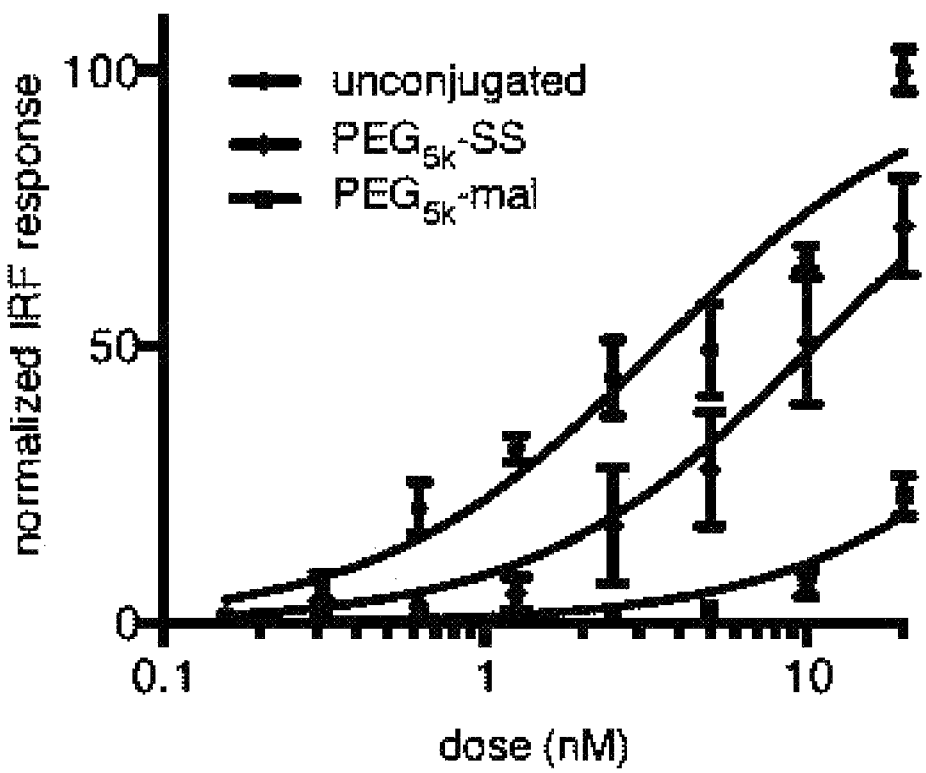
Figure 5D:
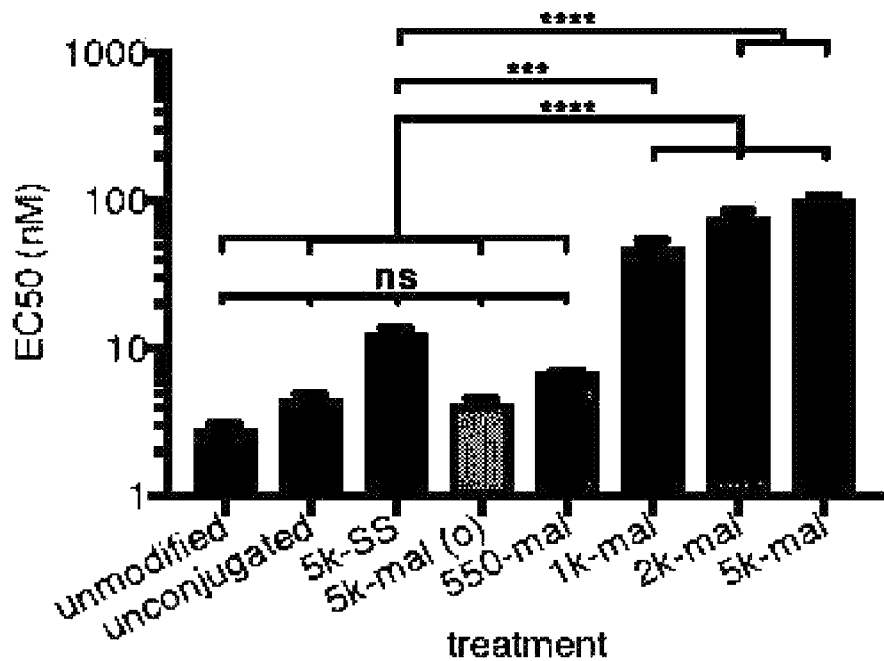

Next, to demonstrate the importance of conjugation site specificity in inhibiting pppRNA activity, 5 kDa PEG was conjugated via a thioester linkage at the 5' end of the strand complementary to the 5'ppp-containing strand such that the PEG was conjugated at the opposite end of the 5'ppp group (FIG. 5B). Equivalent activity was observed between unconjugated pppRNA and pppRNA conjugated with $PEG_{5k}$ on the opposite end, demonstrating that blockade of RIG-I activity with PEG synthetic overhangs requires conjugation on the same end as the 5'ppp group on the dsRNA.

To establish that RIG-I activation could be restored via removal of the overhang, the activity of pppRNA conjugated to $PEG_{5k}$ overhangs via a stable thioester bond or disulfide bridge, which would be anticipated to be cleaved in the reducing environment of the cytosol enabling recognition of pppRNA by RIG-I, was further compared. Indeed, the pppRNA conjugated to PEG via a disulfide was significantly more active than its thioether counterpart (FIG. 5C), though slightly less active than the conjugated pppRNA, which is believed to be a consequence of partial disulfide bond reduction and incomplete liberation of pppRNA from the overhang. To further quantify the effect of molecular weight, conjugation site, and linker chemistry on pppRNA activity, the estimated median effective concentrations (EC50) of the conjugates and relevant controls described above are shown in FIG. 5D.

Finally, as a proof-of-concept demonstration of environmentally-triggerable activation of innate immunity, secretion of human interferon beta (hIFN-β1), a critical mediator of anti-tumor immune responses, by A549 lung cancer cells treated with pppRNA bearing reduction-responsive (disulfide) or non-responsive (maleimide) 5 k D PEG overhangs was quantified. As shown in FIG. 7, only conjugates synthesized with the cleavable disulfide linker were capable of stimulating production of hIFN-β1. While in such an in vitro system removal of the overhang is likely mediated primarily by intracellular glutathione, which has been shown to be elevated in cancer cells, the increased extracellular levels of glutathione associated with tumors might also be exploited to increase ligand activity in the tumor microenvironment prior to cellular entry.

CONCLUSION

This Example demonstrates that synthetic polymer overhangs can be designed to inhibit activation of RIG-I by pppRNA, and that conjugation of synthetic overhangs using environmentally cleavable linkers provides a mechanism for their removal and restoration of pppRNA immunostimulatory properties. This Example also shows that abrogation of activity via synthetic overhangs is at least partially dependent on PEG molecular weight, with a molecular weight of between 550 and 1000 Da being inhibiting RIG-I activity. Furthermore, this Example shows that blockade of RIG-I activity is conjugation site-dependent, as ligation of PEG to the opposite end of the 5' ppp group did not influence ligand activity.

Collectively, this work demonstrates that conjugation of macromolecule overhangs to pppRNA through cleavable linkers is a viable strategy for the development of environmentally triggerable RIG-I-targeting prodrugs. These findings also support the potential to use a diversity of cleavable linker chemistries with sensitivities to different stimuli to create overhangs that can be removed under specific environmental conditions (FIG. 8). For example, in addition to the reduction-sensitive linkage described in this Example, pH labile, reactive oxygen species (ROS) responsive, and/or matrix metalloproteinase cleavable linkers may be employed to synthesize pppRNA-based prodrugs that enrich RIG-I activation in tumors. Moreover, elevated intracellular levels of glutathione, ROS, or enzymatic activity in specific cell populations may be exploited for triggerable RIG-I activation.

Further still, these findings indicate that short PEG overhangs (550 Da) appear to minimally effect RIG-I activation (FIG. 5A), which implies that there is a tolerance for residual overhang material that may remain following linker cleavage. While this phenomenon may be dependent on nature of the linker and overhang chemistry, the data suggest a degree of wiggle room for molecular design of environmentally responsive linkers. Additionally, the dependence of linker chemistry and conjugation site on RIG-I activation have important implications for design of other bioconjugates and prodrugs based on pppRNA, including pppRNA-antibody conjugates for tumor targeting and pppRNA-antigen conjugates for vaccination. Overall, the design of synthetic polymer overhangs for RNA ligands of the RIG-I pathway represents an important development in expanding the utility of this potent and emerging class of PRR agonist. Most importantly, the ability to block RIG-I activation using conjugated synthetic overhangs, but restore activity in an environmentally responsive manner, offers safe and therapeutically relevant prodrugs for localized induction of innate immunity.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

[1] Akira, S.; Uematsu, S.; Takeuchi, O., Pathogen Recognition and Innate Immunity. *Cell* 2006, 124 (4), 783-801.

[2] Mancini, R. J.; Stutts, L.; Ryu, K. A.; Tom, J. K.; Esser-Kahn, A. P., Directing the immune system with chemical compounds. *ACS Chem Biol* 2014, 9 (5), 1075-85.

[3] Lynn, G. M.; Laga, R.; Darrah, P. A.; Ishizuka, A. S.; Balaci, A. J.; Dulcey, A. E.; Pechar, M.; Pola, R.; Gerner, M. Y.; Yamamoto, A.; Buechler, C. R.; Quinn, K. M.; Smelkinson, M. G.; Vanek, O.; Cawood, R.; Hills, T.; Vasalatiy, O.; Kastenmuller, K.; Francica, J. R.; Stutts, L.; Tom, J. K.; Ryu, K. A.; Esser-Kahn, A. P.; Etrych, T.; Fisher, K. D.; Seymour, L. W.; Seder, R. A., In vivo characterization of the physicochemical properties of polymer-linked TLR agonists that enhance vaccine immunogenicity. *Nat Biotechnol* 2015, 33 (11), 1201-10.

[4] Gutjahr, A.; Tiraby, G.; Perouzel, E.; Verrier, B.; Paul, S., Triggering Intracellular Receptors for Vaccine Adjuvantation. *Trends Immunol* 2016, 37 (9), 573-87.

[5] Maisonneuve, C.; Bertholet, S.; Philpott, D. J.; De Gregorio, E., Unleashing the potential of NOD- and Toll-like agonists as vaccine adjuvants. *Proceedings of the National Academy of Sciences of the U.S. Pat. No.* 2,014,111 (34), 12294-12299.

[6] van den Boorn, J. G.; Hartmann, G., Turning Tumors into Vaccines: Co-opting the Innate Immune System. *Immunity* 2013.

[7] Moynihan, K. D.; Irvine, D. J., Roles for Innate Immunity in Combination Immunotherapies. *Cancer Res* 2017, 77 (19), 5215-5221.

[8] Fiuza, C.; Suffredini, A. F., Human models of innate immunity: local and systemic inflammatory responses. *Journal of Endotoxin Research* 2001, 7 (5), 385-388.

[9] Copin, R.; Vitry, M. A.; Hanot Mambres, D.; Machelart, A.; De Trez, C.; Vanderwinden, J. M.; Magez, S.; Akira, S.; Ryffel, B.; Carlier, Y.; Letesson, J. J.; Muraille, E., In situ microscopy analysis reveals local innate immune response developed around *Brucella* infected cells in resistant and susceptible mice. *PLoS Pathog* 2012, 8 (3), e1002575.

[10] Liang, F.; Lore, K., Local innate immune responses in the vaccine adjuvant-injected muscle. *Clin Transl Immunology* 2016, 5 (4), e74.

[11] Tang, D. L.; Kang, R.; Coyne, C. B.; Zeh, H. J.; Lotze, M. T., PAMPs and DAMPs: signal Os that spur autophagy and immunity. *Immunological Reviews* 2012, 249 (1600-065X (Electronic)), 158-175.

[12] Appelbe, O. K.; Moynihan, K. D.; Flor, A.; Rymut, N.; Irvine, D. J.; Kron, S. J., Radiation-enhanced delivery of systemically administered amphiphilic-CpG oligodeoxynucleotide. *J Control Release* 2017, 266, 248-255.

[13] Dudek, A. Z.; Yunis, C.; Harrison, L. I.; Kumar, S.; Hawkinson, R.; Cooley, S.; Vasilakos, J. P.; Gorski, K. S.; Miller, J. S., First in human phase I trial of 852A, a novel systemic toll-like receptor 7 agonist, to activate innate immune responses in patients with advanced cancer. *Clin Cancer Res* 2007, 13 (23), 7119-25.

[14] Campanelli, A.; Krischer, J.; Saurat, J. H., Topical application of imiquimod and associated fever in children. *J Am Acad Dermatol* 2005, 52 (1), E1.

[15] Savage, P.; Horton, V.; Moore, J.; Owens, M.; Witt, P.; Gore, M. E., A phase I clinical trial of imiquimod, an oral interferon inducer, administered daily. *Br J Cancer* 1996, 74 (9), 1482-6.

[16] Engel, A. L.; Holt, G. E.; Lu, H., The pharmacokinetics of Toll-like receptor agonists and the impact on the immune system. *Expert Rev Clin Pharmacol* 2011, 4 (2), 275-89.

[17] Vasou, A.; Sultanoglu, N.; Goodbourn, S.; Randall, R. E.; Kostrikis, L. G., Targeting Pattern Recognition Receptors (PRR) for Vaccine Adjuvantation: From Synthetic PRR Agonists to the Potential of Defective Interfering Particles of Viruses. *Viruses* 2017, 9 (7).

[18] Broz, P.; Monack, D. M., Newly described pattern recognition receptors team up against intracellular pathogens. *Nature Reviews Immunology* 2013, 13 (8), 551-565.

[19] Iwasaki, A.; Medzhitov, R., Toll-like receptor control of the adaptive immune responses. *Nat Immunol* 2004, 5 (10), 987-95.

[20] Kuai, R.; Ochyl, L. J.; Bahjat, K. S.; Schwendeman, A.; Moon, J. J., Designer vaccine nanodiscs for personalized cancer immunotherapy. *Nat Mater* 2017, 16 (4), 489-496.

[21] Tom, J. K.; Dotsey, E. Y.; Wong, H. Y.; Stuns, L.; Moore, T.; Davies, D. H.; Felgner, P. L.; Esser-Kahn, A. P., Modulation of Innate Immune Responses via Covalently Linked TLR Agonists. *ACS Cent Sci* 2015, 1 (8), 439-448.

[22] Liu, H.; Moynihan, K. D.; Zheng, Y.; Szeto, G. L.; Li, A. V.; Huang, B.; Van Egeren, D. S.; Park, C.; Irvine, D. J., Structure-based programming of lymph-node targeting in molecular vaccines. *Nature* 2014, 507 (7493), 519-522.

[23] Corrales, L.; Glickman, L. H.; McWhirter, S. M.; Kanne, D. B.; Sivick, K. E.; Katibah, G. E.; Woo, S. R.; Lemmens, E.; Banda, T.; Leong, J. J.; Metchette, K.; Dubensky, T. W., Jr.; Gajewski, T. F., Direct Activation of STING in the Tumor Microenvironment Leads to Potent and Systemic Tumor Regression and Immunity. *Cell Rep* 2015, 11 (7), 1018-30.

[24] Zhang, P.; Chiu, Y. C.; Tostanoski, L. H.; Jewell, C. M., Polyelectrolyte Multilayers Assembled Entirely from Immune Signals on Gold Nanoparticle Templates Promote Antigen-Specific T Cell Response. *ACS Nano* 2015, 9 (6), 6465-77.

[25] He, S.; Mao, X.; Sun, H.; Shirakawa, T.; Zhang, H.; Wang, X., Potential therapeutic targets in the process of nucleic acid recognition: opportunities and challenges. *Trends Pharmacol Sci* 2015, 36 (1), 51-64.

[26] Schlee, M., Master sensors of pathogenic RNA-RIG-I like receptors. *Immunobiology* 2013, 218 (11), 1322-35.

[27] Kell, A. M.; Gale, M., Jr., RIG-I in RNA virus recognition. *Virology* 2015, 479-480, 11021.

[28] Hornung, V.; Ellegast, J.; Kim, S.; Brzozka, K.; Jung, A.; Kato, H.; Poeck, H.; Akira, S.; Conzelmann, K. K.; Schlee, M.; Endres, S.; Hartmann, G., 5'-Triphosphate RNA Is the Ligand for RIG-I. *Science* 2006, 314 (5801), 994-997.

[29] Goulet, M.-L.; Olagnier, D.; Xu, Z.; Paz, S.; Belgnaoui, S. M.; Lafferty, E. I.; Janelle, V.; Arguello, M.; Paquet, M.; Ghneim, K.; Richards, S.; Smith, A.; Wilkinson, P.; Cameron, M.; Kalinke, U.; Qureshi, S.; Lamarre, A.; Haddad, E. K.; Sekaly, R. P.; Peri, S.; Balachandran, S.; Lin, R.; Hiscott, J., Systems analysis of a RIG-I agonist inducing broad spectrum inhibition of virus infectivity. *PLoS pathogens* 2013, 9 (4), e1003298.

[30] Kohlway, A.; Luo, D.; Rawling, D. C.; Ding, S. C.; Pyle, A. M., Defining the functional determinants for RNA surveillance by RIG-I. *EMBO reports* 2013, 14 (9), 772-779.

[31] Parker, B. S.; Rautela, J.; Hertzog, P. J., Antitumour actions of interferons: implications for cancer therapy. *Nat Rev Cancer* 2016, 16 (3), 131-44.

[32] Harlin, H.; Meng, Y.; Peterson, A. C.; Zha, Y.; Tretiakova, M.; Slingluff, C.; McKee, M.; Gajewski, T. F., Chemokine expression in melanoma metastases associated with CD8+ T-cell recruitment. *Cancer Res* 2009, 69 (7), 3077-85.

[33] Gajewski, T. F., The Next Hurdle in Cancer Immunotherapy: Overcoming the Non-T-Cell-Inflamed Tumor Microenvironment. *Semin Oncol* 2015, 42 (4), 663-71.

[34] Ellermeier, J.; Wei, J.; Duewell, P.; Hoves, S.; Stieg, M. R.; Adunka, T.; Noerenberg, D.; Anders, H. J.; Mayr, D.; Poeck, H.; Hartmann, G.; Endres, S.; Schnurr, M., Therapeutic Efficacy of Bifunctional siRNA Combining TGF-beta1 Silencing with RIG-I Activation in Pancreatic Cancer. *Cancer Research* 2013, 73 (6), 1709-1720.

[35] Duewell, P.; Steger, A.; Lohr, H.; Bourhis, H.; Hoelz, H.; Kirchleitner, S. V.; Stieg, M. R.; Grassmann, S.; Kobold, S.; Siveke, J. T.; Endres, S.; Schnurr, M., RIG-I-like helicases induce immunogenic cell death of pancreatic cancer cells and sensitize tumors toward killing by CD8(+) T cells. *Cell Death Differ* 2014, 21 (12), 1825-37.

[36] Poeck, H.; Besch, R.; Maihoefer, C.; Renn, M.; Tormo, D.; Morskaya, S. S.; Kirschnek, S.; Gaffal, E.; Landsberg, J.; Hellmuth, J.; Schmidt, A.; Anz, D.; Bscheider, M.; Schwerd, T.; Berking, C.; Bourquin, C.; Kalinke, U.; Kremmer, E.; Kato, H.; Akira, S.; Meyers, R.; Hacker, G.; Neuenhahn, M.; Busch, D.; Ruland, J.; Rothenfusser, S.; Prinz, M.; Hornung, V.; Endres, S.; Tilting, T.; Hartmann, G., 5'-triphosphate-siRNA: turning gene silencing and RIG-I activation against melanoma. *Nature Medicine* 2008, 14 (11), 1256-1263.

[37] Robert Besch, H. P. T. H. D. S. G. H. C. B. V. H. S. E. T. R. S. R. G. H., Proapoptotic signaling induced by RIG-I and MDA-5 results in type I interferon-independent apoptosis in human melanoma cells. *The Journal of clinical investigation* 2009, 119 (8), 2399.

[38] Matsushima-Miyagi, T.; Hatano, K.; Nomura, M.; Li-Wen, L.; Nishikawa, T.; Saga, K.; Shimbo, T.; Kaneda, Y., TRAIL and Noxa are selectively upregulated in prostate cancer cells downstream of the RIG-I/MAVS signaling pathway by nonreplicating Sendai virus particles. *Clin Cancer Res* 2012, 18 (22), 6271-83.

[39] Schock, S. N.; Chandra, N. V.; Sun, Y.; Irie, T.; Kitagawa, Y.; Gotoh, B.; Coscoy, L.; Winoto, A., Induction of necroptotic cell death by viral activation of the RIG-I or STING pathway. *Cell Death Differ* 2017, 24 (4), 615-625.

[40] Yuan, D.; Xia, M.; Meng, G.; Xu, C.; Song, Y.; Wei, J., Anti-angiogenic efficacy of 5'-triphosphate siRNA combining VEGF silencing and RIG-I activation in NSCLCs. *Oncotarget* 2015, 6 (30), 29664-74.

[41] Krieg, A. M., Therapeutic potential of Toll-like receptor 9 activation. *Nature Reviews Drug Discovery* 2006, 5 (6), 471-484.

[42] Marq, J.-B.; Kolakofsky, D.; Garcin, D., Unpaired 5' ppp-Nucleotides, as Found in Arenavirus Double-stranded RNA Panhandles, Are Not Recognized by RIG-I. *The Journal of Biological Chemistry* 2010, 285 (24), 18208-18216.

[43] Chan, Y. K.; Gack, M. U., Viral evasion of intracellular DNA and RNA sensing. *Nat Rev Microbiol* 2016, 14 (6), 360-73.

[44] Alconcel, S. N. S.; Baas, A. S.; Maynard, H. D., FDA-approved poly(ethylene glycol)-protein conjugate drugs. *Polymer Chemistry* 2011, 2 (7), 1442-1448.

[45] Zhang, Y.; Zhang, Y. F.; Bryant, J.; Charles, A.; Boado, R. J.; Pardridge, W. M., Intravenous RNA interference gene therapy targeting the human epidermal growth factor receptor prolongs survival in intracranial brain cancer. *Clin Cancer Res* 2004, 10 (11), 3667-77.

[46] Xia, C. F.; Zhang, Y.; Zhang, Y.; Boado, R. J.; Pardridge, W. M., Intravenous siRNA of brain cancer with receptor targeting and avidin-biotin technology. *Pharm Res* 2007, 24 (12), 2309-16.

[47] Gunasekaran, K.; Nguyen, T. H.; Maynard, H. D.; Davis, T. P.; Bulmus, V., Conjugation of siRNA with comb-type PEG enhances serum stability and gene silencing efficiency. *Macromol Rapid Commun* 2011, 32 (8), 654-9.

[48] Kanasty, R.; Dorkin, J. R.; Vegas, A.; Anderson, D., Delivery materials for siRNA therapeutics. *Nature Materials* 2013, 12 (11), 967-977.

[49] Oishi, M.; Nagasaki, Y.; Itaka, K.; Nishiyama, N.; Kataoka, K., Lactosylated Poly(ethylene glycol)-siRNA Conjugate through Acid-Labile β-Thiopropionate Linkage to Construct pH-Sensitive Polyion Complex Micelles Achieving Enhanced Gene Silencing in Hepatoma Cells. *Journal of the American Chemical Society* 2005, 127 (6), 1624-1625.

[50] Jeong, J. H.; Mok, H.; Oh, Y.-K.; Park, T. G., siRNA Conjugate Delivery Systems. *Bioconjugate Chemistry* 2009, 20 (1), 5-14.

[51] Schafer, F. Q.; Buettner, G. R., Redox environment of the cell as viewed through the redox state of the glutathione disulfide/glutathione couple. *Free Radical Biology and Medicine* 2001, 30 (11), 1191-1212.

[52] Schlee, M.; Roth, A.; Hornung, V.; Hagmann, C. A.; Wimmenauer, V.; Barchet, W.; Coch, C.; Janke, M.; Mihailovic, A.; Wardle, G.; Juranek, S.; Kato, H.; Kawai, T.; Poeck, H.; Fitzgerald, K. A.; Takeuchi, O.; Akira, S.; Tuschl, T.; Latz, E.; Ludwig, J.; Hartmann, G., Recognition of 5' Triphosphate by RIG-I Helicase Requires Short Blunt Double-Stranded RNA as Contained in Panhandle of Negative-Strand Virus. *Immunity* 2009, 31 (1), 25-34.

[53] Zitvogel, L.; Galluzzi, L.; Kepp, O.; Smyth, M. J.; Kroemer, G., Type I interferons in anticancer immunity. *Nat Rev Immunol* 2015, 15 (7), 405-14.

[54] Gamcsik, M. P.; Kasibhatla, M. S.; Teeter, S. D.; Colvin, O. M., Glutathione levels in human tumors. *Biomarkers* 2012, 17 (8), 671-91.

[55] Balendiran, G. K.; Dabur, R.; Fraser, D., The role of glutathione in cancer. *Cell Biochemistry and Function* 2004, 22 (6), 343-352.

[56] MacEwan, S. R.; Callahan, D. J.; Chilkoti, A., Stimulus-responsive macromolecules and nanoparticles for cancer drug delivery. *Nanomedicine (Loud)* 2010, 5 (5), 793-806.

[57] Zhu, L.; Torchilin, V. P., Stimulus-responsive nano-preparations for tumor targeting. *Integr Biol (Camb)* 2013, 5 (1), 96-107.

[58] Zlatev, I.; Manoharan, M.; Vasseur, J. J.; Morvan, F., Solid-phase chemical synthesis of 5'-triphosphate DNA, RNA, and chemically modified oligonucleotides. *Curr Protoc Nucleic Acid Chem* 2012, Chapter 1, Unit1 28.

[59] Wincott, F.; DiRenzo, A.; Shaffer, C.; Grimm, S.; Tracz, D.; Workman, C.; Sweedler, D.; Gonzalez, C.; Scaringe, S.; Usman, N., Synthesis, deprotection, analysis and purification of RNA and ribozymes. *Nucleic Acids Res* 1995, 23 (14), 2677-84.

[60] Tuschl, T.; Eckstein, F., Hammerhead ribozymes: importance of stem-loop II for activity. *Proc Natl Acad Sci USA* 1993, 90 (15), 6991-4.

[61] John C. Lindon, G. E. T., David Koppenaal, *Encylopedia of Spectroscopy and Spectrometry*. 3 ed.; 2016; p 3584.

[62] Linehan, M.; Dickey, T.; Molinari, E.; Fitzgerald, M.; Potapova, O.; Iwasaki, A.; Pyle, A., A minimial RNA ligand for potent RIG-I activation in living mice. *bioRxiv* 2017, 178343.

[63] Kohlway, A.; Luo, D.; Rawling, D.; Ding, S.; Pyle, A., Defining the functional determinants for RNA surveillance by RIG-I. *EMBO reports* 2013, 14 (9) 772-779.

[64] Goldeck, M.; Tuschl, T.; Hartmann, G.; Ludwig, J., Efficient Solid-Phase Synthesis of pppRNA by Using Product-Specific Labeling. *Angew. Chem. Int. Ed.* 2014, 53, 4694-4698.

[65] U.S. Pat. No. 9,695,212 B2

[66] McCombs, J. R.; Owen, S. C., Antibody Drug Conjugates: Design and Selection of Linker, Payload and Conjugation Chemistry. *The AAPS Journal* 2015, 17 (2), 339-351.

[67] Saneyoshi, H.; Yamamoto, Y.; Kondo, K.; Hiyoshi, Y.; Ono, A., Conjugatable and Bioreduction Cleavable Linker for the 5'-Functionalization of Oligonucleotides. *J Org Chem* 2017, 82 (3), 1796-1802.

[68] Saravanakumar, G.; Kim, J.; Kim, W. J., Reactive-Oxygen-Species-Responsive Drug Delivery Systems: Promises and Challenges. *Adv Sci (Weinh)* 2017, 4 (1), 1600124.

[69] Desnoyers, L. R.; Vasiljeva, O.; Richardson, J. H.; Yang, A.; Menendez, E. E.; Liang, T. W.; Wong, C.; Bessette, P. H.; Kamath, K.; Moore, S. J.; Sagert, J. G.; Hostetter, D. R.; Han, F.; Gee, J.; Flandez, J.; Markham, K.; Nguyen, M.; Krimm, M.; Wong, K. R.; Liu, S.; Daugherty, P. S.; West, J. W.; Lowman, H. B., Tumor-specific activation of an EGFR-targeting probody enhances therapeutic index. *Sci Transl Med* 2013, 5 (207), 207ra144.

[70] Ryu, K. A.; McGonnigal, B.; Moore, T.; Kargupta, T.; Mancini, R. J.; Esser-Kahn, A. P., Light Guided In-vivo Activation of Innate Immune Cells with Photocaged TLR 2/6 Agonist. *Sci Rep* 2017, 7 (1), 8074.

[71] Stutts, L.; Esser-Kahn, A. P., A Light-Controlled TLR4 Agonist and Selectable Activation of Cell Subpopulations. *Chembiochem* 2015, 16 (12), 1744-8.

[72] Hang, C.; Zou, Y.; Zhong, Y.; Zhong, Z.; Meng, F., NIR and UV-responsive degradable hyaluronic acid nanogels for CD44-targeted and remotely triggered intracellular doxorubicin delivery. *Colloids Surf B Biointerfaces* 2017, 158 (1873-4367 (Electronic)), 547-555.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

What is claimed is:

1. A selective pattern recognition receptor (PRR) agonist, comprising:

a nucleic acid agonist; and a macromolecule conjugated to the nucleic acid agonist, wherein the macromolecule has a molecular weight of at least 550 Da, and removal of at least a portion of the macromolecule permits binding of the agonist to a PRR.

2. The selective PRR agonist of claim 1, wherein the nucleic acid agonist comprises a nucleic acid duplex having at least two phosphoryl groups attached to a 5' end thereof.

3. The selective PRR agonist of claim 2, wherein the nucleic acid duplex comprises a double stranded nucleic acid molecule.

4. The selective PRR agonist of claim 2, wherein the nucleic acid duplex comprises a single-stranded nucleic acid molecule.

5. The selective PRR agonist of claim 4, wherein the single-stranded nucleic acid molecule comprises a hairpin loop RNA molecule.

6. The selective PRR agonist of claim 2, wherein the at least two phosphoryl groups are selected from the group consisting of a diphosphate group and a triphosphate group.

7. The selective PRR agonist of claim 1, further comprising an environmentally selective linker conjugating the macromolecule to the nucleic acid agonist.

8. The selective PRR agonist of claim 7, wherein the environmentally selective linker is selected from the group consisting of reactive oxygen species (ROS) sensitive linking agents, pH sensitive linking agents, redox sensitive linking agents, enzymatically cleavable linking agents, light sensitive linking agents, and combinations thereof.

9. The selective PRR agonist of claim 8, wherein the redox sensitive linking agents are selected from the group consisting of glutathione sensitive linkers, nitroreductase/NADH sensitive linkers, and combinations thereof.

10. The selective PRR agonist of claim 8, wherein the pH sensitive linking agents are selected from the group consisting of hydrazone, silyl ethers, other low pH sensitive linking agents, and combinations thereof.

11. The selective PRR agonist of claim 8, wherein the enzymatically cleavable linking agents are selected from the group consisting of matrix metalloproteinases, dipeptide/p-aminobenzyl alcohol systems, lysosomal, beta-glucuronidase, intracellular esterases, and combinations thereof.

12. The selective PRR agonist of claim 2, wherein the macromolecule is conjugated to a 3' end of the nucleic acid duplex, the 3' end that the macromolecule is conjugated to and the 5' end that the at least two phosphoryl groups are attached to being at a single terminus of the nucleic acid duplex.

13. The selective PRR agonist of claim 12, wherein the agonist is a retinoic acid-inducible gene I (RIG-I) agonist.

14. The selective PRR agonist of claim 2, wherein the macromolecule is conjugated to one of the phosphoryl groups attached to the 5' end of the nucleic acid duplex.

15. A method of selectively activating a pattern recognition receptor (PRR), the method comprising:
   administering the selective PRR agonist of claim 1 to a subject; and
   cleaving at least a portion of the macromolecule conjugated to the nucleic acid agonist;
   wherein the cleaving of at least a portion of the macromolecule permits the agonist to bind a PRR.

16. The method of claim 15, further comprising an environmentally selective linker conjugating the macromolecule to the nucleic acid agonist.

17. The method of claim 16, wherein the cleaving step comprises passively or actively subjecting the agonist to an environmental stimulus corresponding to the environmentally selective linker.

18. The method of claim 15, further comprising a carrier system attached to the agonist.

* * * * *

SEQUENCE LISTING

<160> NUMBER OF SEQ ID NOS: 2

<210> SEQ ID NO 1
<211> LENGTH: 25
<212> TYPE: RNA
<213> ORGANISM: Artificial
<220> FEATURE:
<223> OTHER INFORMATION: Synthetic RNA strand

<400> SEQUENCE: 1
cguuaaucgc guauaauacg ccuau 25

<210> SEQ ID NO 2
<211> LENGTH: 25
<212> TYPE: RNA
<213> ORGANISM: Artificial
<220> FEATURE:
<223> OTHER INFORMATION: Synthetic RNA strand

<400> SEQUENCE: 2
auaggcguau uauacgcgau uaacg 25